US006004782A

United States Patent [19]
Daniell et al.

[11] Patent Number: 6,004,782
[45] Date of Patent: Dec. 21, 1999

[54] HYPEREXPRESSION OF BIOELASTIC POLYPEPTIDES

[75] Inventors: Henry Daniell, Auburn; David T. McPherson, Birmingham; Dan W. Urry, Birmingham; Jie Xu, Birmingham, all of Ala.

[73] Assignees: Bioelastics Research Ltd.; The UAB Research Foundation, both of Birmingham, Ala.

[21] Appl. No.: 08/542,051

[22] Filed: Oct. 13, 1995

Related U.S. Application Data

[63] Continuation of application No. 08/423,642, Apr. 14, 1995, abandoned.

[51] Int. Cl.$^6$ .............................. C12N 1/20; C12N 1/21; C12N 15/11; C12P 21/02
[52] U.S. Cl. ...................... 435/71.2; 435/69.1; 435/69.7; 435/252.3; 536/23.1; 536/23.4; 530/300; 530/350
[58] Field of Search .................................. 435/325, 69.7, 435/69.1, 172.3, 410, 414, 252.3; 536/23.1, 23.4; 530/300, 350

[56] References Cited

U.S. PATENT DOCUMENTS

| | | | |
|---|---|---|---|
| 4,132,746 | 1/1979 | Urry et al. | 260/857 |
| 4,187,852 | 2/1980 | Urry et al. | 128/334 |
| 4,474,851 | 10/1984 | Urry | 428/373 |
| 4,500,700 | 2/1985 | Urry | 528/328 |
| 4,589,882 | 5/1986 | Urry | 623/11 |
| 4,605,413 | 8/1986 | Urry et al. | 623/11 |
| 4,693,718 | 9/1987 | Urry et al. | 623/11 |
| 4,783,523 | 11/1988 | Urry et al. | 530/323 |
| 4,870,055 | 9/1989 | Urry et al. | 514/12 |
| 4,898,926 | 2/1990 | Urry | 528/328 |
| 4,952,496 | 8/1990 | Studier et al. | 435/91 |
| 4,976,734 | 12/1990 | Urry et al. | 623/11 |
| 5,032,271 | 7/1991 | Urry | 210/350 |
| 5,064,430 | 11/1991 | Urry | 623/1 |
| 5,085,055 | 2/1992 | Urry | 60/527 |
| 5,226,292 | 7/1993 | Urry | 60/712 |
| 5,250,516 | 10/1993 | Urry | 514/17 |
| 5,255,518 | 10/1993 | Urry | 60/527 |

OTHER PUBLICATIONS

Bitter Methods in Enzymology vol. 152 673–684, 1987.
Zhang et al BioTechnology Letters vol. 17 No. 12 1279–1284, Dec. 1995.
Grosso et al Matrix vol. 13 (2) 157–164, 1993.
Salerno et al Polym Mater Sci Eng vol. 33 p. 398, 1992.
Kuliopulos et al J Am Chem Soc vol. 116 4599–4607, 1994.
Firek et al Plant Molecular Biology vol. 23 861–870, 1993.
Kelley et al Gene vol. 156 33–36.
Mertens et al Bio/Technology vol. 13 175–179, Feb. 1995.
Kane et al Trends In Biotechnology vol. 6 95–101, 1988.
Brosius, (1984) "Plasmid Vectors for the Selection of Promoters" *Gene* 27:151–160.

Brosius, (1984) "Toxicity of an Overproduced Foreign Gene Product in *Escherichia coli* and Its Use In Plasmid Vectors for the Selection of Transcription Terminators" *Gene* 27:161–172.
Daniell et al., (1994) "Engineering Plants for Stress Tolerance via Organelle Genomes" in *Biochemical and Cellular Mechanisms of Stress Tolerance in Plants*, J.H. Cherry, Ed. (Springer Verlag, NY) pp. 589–604.
Dubendorff and Studier, (1991) "Controlling Basal Expression in an Inducible T7 Expression System by Blocking the Targer T7 Promoter with lac Repressor" *J. Mol. Biol* 19:45–59.
Gribskov and Burgess, (1983) "Overexpression and Purification of the Sigman Subunit of *Escherichia coli* RNA Polymerase" *Gene* 26:109–118.
Hartley and Kane, (1988) "Recovery and Reactivation of Recombinant Proteins" *Biochemical Society Transactions* 16:101–102.
Kane and Hartley, (1988) "Formation of Recombinant Protein Inclusion Bodies in *Escherichia coli*" *Tibech* 6:95–101.
Masiu, et al., (1984) "Novel High–Level Expression Cloning Vehicles: $10^4$–Fold Amplification of *Escherichia coli* Minor Protein" *Biotechnology* 2:81–85.
McPherson et al., (1992) "Production and Purification of a Recombinant Elastomeric Polypeptide, G–(VPGVG)$_{19}$–VPGV, from *Escherichia coli*."*Biotechnol. Prog.* 8:347–352.
Rapaka et al., (1978) "Coacervation Properties in Sequential Polypeptide Models of Elastin" *Int. J. Peptide Protein Res.* 12:81–92.
Rosenberg et al., (1987) "Vectors for Selective Expression of cloned DNAs by T7 RNA Polymerase" *Gene* 56:125–135.
Schoner, et al., (1985) "Isolation and Purification of Protein Granules From *Escherichia coli* Cells Overproducing Bovine Growth Hormone" *Biotechnology* 3:151–154.
Studier et al., (1990) "Use of T7 RNA Polymerase to Direct Expression of Cloned Genes" *Methods in Enzymology* 185:60–89.
Studier et al., (1986) "Use of Bacteriophage T7 RNA polymerase to Direct Selective High–level Expression of Cloned Genes" *J. Mol. Biol.* 189:113–130.
Studier, F.W., (1991) "Use of Bacteriophage T7 Lysozyme to Improve and Inducible T7 Expression System" *J. Mol. Biol.* 219:37–44.

(List continued on next page.)

Primary Examiner—Julie Reeves
Attorney, Agent, or Firm—Cooley Godward LLP

[57] ABSTRACT

A method for overexpressing a bioelastic polypeptide in a host cell is provided. A nucleic acid encoding a bioelastic polypeptide having pentapeptide, tetrapeptide, hexapeptide or nonapeptide repeating units is introduced into a host cell. The host cell is grown under conditions that provide for expression of the polypeptide as at least 40% of the total cellular protein of the host cell.

6 Claims, 8 Drawing Sheets

OTHER PUBLICATIONS

Tartof and Hobbs, (1987) "Improved Media for Growing Plasmid and Cosmid Clones" *Besthesda Res. Lab. Focus* 9:12.

Urry et al., (1985) "Carbon–13 NMR Relaxation Studies Demonstrate and Inverse Temperature Transition in the Elastin Polypentapeptide" *Biochemistry* 24:5182–5188.

Urry et al., (1992) "Hydrophobicity Scale for Proteins Based on Inverse Temperature Transitions" *Biopolymers* 32:1243–1250.

Urry, (1993) "Molecular Machines: How Motion and Other Functions of Living Organisms Can Result From Reversible Chemical Changes" *Angewandte Chemie: A Journal of the Gesellschaft Deutscher Chemiker* 32 (6) :819–841.

Urry, et al., (1992) "Design at Nanometric Dimensions To Enhance Hydrophobicity–Induced $pK_a$ Shifts" *J. Am. Chem. Soc.* 114:8716–8717.

Urry, et al., (1993) "Delineation of Electrostatic– and Hydrophobic–Induced $pK_a$ Shifts in Polypentapeptides: The Glutamic Acid Residue" *J. Am. Chem. Soc.* 115:7509–7510.

Urry et al., (1991) "Poly ($Val^1$–$Pro^2$–$Ala^3Val^4$–$Gly^5$): A Reversible, Inverse Thermoplastic" in *Biotechnology and Polymers,* C.G. Gebelin, ed. (Plenum Press, NY) pp. 265–274.

Urry et al., (1993) "Medical Applications of Bioelastic Materials" in *Biotechnological Polymers: Medical, Pharmaceutical and Industrial Applications,* pp. 82–103.

Williams, et al., (1982) "Cytoplasmic Inclusion Bodies in *Escherichia coli* Producing Biosynthetic Human Insulin Proteins" *Science* 215:687–689.

Novagen Catalogue (1995) pp. 10, 24–29, 31, 58–62, 78–95.

Urry et al., Protein–Based Polymeric Materials (Synthesis and Properties), pp. 7263–7279, (1996).

Zhang et al., "Nuclear Expression of an Environmentally Friendly Synthetic Protein Based Polymer Gene in Tobacco Cells," Biotechnology Letters, vol. 17(12):1279–1284 (1985).

Figure 1A

```
              P    G    V    G    V    P    G    V
             Pf1M1
cgggat   CCA GGA GTT GGA GTT CCT
gcccta   GGT CCT CAA CCT CAA GGA
    BamH 1

GGT GTA GGT GTA CCT
         CCA CAT CCA CAT GGA

GGA GTT GGT GTA CCT
         CCT CAA CCA CAT GGA

GGT GTA GGA GTT CCT
         CCA CAT CCT CAA GGA

GGA GTT GGT GTT CCA
         CCT CAA CCA CAA GGT
                     Kpnl
         GGT GTA GGG GTA CCT
         CCA CAT CCC CAT GGA

GGT GTT GGT GTT CCT
         CCA CAA CCA CAA GGA

GGA GTA GGA GTA CCT
         CCT CAT CCT CAT GGA

GGT GTT GGA GTA CCC
         CCA CAA CCT CAT GGG
    Sma I                    Pf1M1
         GGG GTA GGT GTT CCA GGA GTT GG    atcccg
         CCC CAT CCA CAA GGT CCT CAA CC    tagggc
                                            BamH 1
```

Figure 3 a. (AVGVP)₁₀ gene

```
         ala val gly val pro ala val gly val pro
BamH 1   PfIH 1
gaggatcca GCT GTT GGT GTT CCG GCA GTA GGC GTA CCG
          GCT GTT GGC GTA CCG GCA GTA GGT GTT CCG
          GCG GTT GGT GTG CCG GCT GTA GGC GTT CCG
          GCA GTT GGT GTA CCG GCG GTA GGC GTT CCG
          GCT GTG GGT GTA CCG GCA GTT GGC GTT CCA gctgttggatccag
                                                  PfIH 1   BamH 1
```

Figure 5A b. (GGAP)₁₂ gene

```
            gly gly ala pro gly gly gly ala pro
BamH 1 Bbs 1
gaggatccgaagaca GGT GGT GCT CCG GGC GGC GCA CCG
                GGT GGC GCT CCG GGC GGT GCC CCG
                GGA GGT GCT CCG GGT GGG GCG CCA
                GGC GGT GCT CCG GGA GGG CCG
                GGC GGT GCA CCG GGT GGG GCT CCG
                GGT GGC GCA CCG GGC GGT GCG CCA ggaagtcttcggatccag
                                                 Bbs 1   BamH 1
```

Figure 5B a. AVGVP adaptor oligos

5'

```
              met gly lys gly lys ala pro gly lys ala val
gaggatccagacc ATG GGT AAA GGA AAA GCA CCG GGT AAA GCG C
ctcctaggtctgg TAC CCA TTT CCT TTT CGT GGC CCA TTT CGC GGT CC
      BamH 1  Nco 1
```

3'

```
val gly val pro stop
 TT GGT GTT CCG TAA gcttgaattcggatccag
 GA CCA CAA GGC ATT cgaacttaagcctaggtc
                   Hind 3  EcoR 1  BamH 1
``` b. GGAP adaptor oligos

5'

```
         met gly lys gly lys ala pro gly lys ala pro
gaggatcc ATG GGT AAA GGA AAA GCA CCG GGT AAA GCG C
ctcctagg TAC CCA TTT CCT TTT CGT GGC CCA TTT CGC GGT CC
BamH 1   Nco 1
```

3'

```
gly gly ala pro stop
CA GGT GGT GCT CCG TAA gcttgaattcggatccag
 A CCA CGA GGC ATT     cgaacttaagcctaggtc
                       Hind 3  EcoR 1  BamH 1
```

Figure 6

SEQUENCE LISTING

<160> NUMBER OF SEQ ID NOS: 50

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence:synthetic

<400> SEQUENCE: 1

Val Pro Gly Val Gly
 1               5

```
<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence:synthetic

<400> SEQUENCE: 2

Val Ala Pro Gly Val Gly
 1               5

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence:synthetic

<400> SEQUENCE: 3

Val Pro Gly Gly
 1

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence:synthetic

<400> SEQUENCE: 4

Val Pro Ala Val Gly
 1               5

<210> SEQ ID NO 5
<211> LENGTH: 173
<212> TYPE: DNA
<213> ORGANISM: Artificial Sequence
<220> FEATURE:
<223> OTHER INFORMATION: Description of Artificial Sequence:synthetic

<400> SEQUENCE: 5
cgggatccag gagttggagt tcctggtgta ggtgtacctg gagttggtgt acctggtgta      60
ggagttcctg gagttggtgt tccaggtgta ggggtacctg gtgttggtgt tcctggagta     120
ggagtacctg gtgttggagt acccggggta ggtgttccag gagttggatc ccg            173

<210> SEQ ID NO 6
<211> LENGTH: 173
<212> TYPE: DNA
<213> ORGANISM: Artificial Sequence
<220> FEATURE:
<223> OTHER INFORMATION: Description of Artificial Sequence:synthetic

<400> SEQUENCE: 6
gaggatccag ctgttggtgt tccggcagta ggcgtaccgg ctgttggcgt accggcagta      60
ggtgttccgg cggttggtgt gccggctgta ggcgttccgg cagttggtgt accggcggta     120
ggcgttccgg ctgtgggtgt accggcagtt ggcgttccag ctgttggatc cag            173

<210> SEQ ID NO 7
<211> LENGTH: 177
<212> TYPE: DNA
<213> ORGANISM: Artificial Sequence
<220> FEATURE:
<223> OTHER INFORMATION: Description of Artificial Sequence:synthetic

<400> SEQUENCE: 7
```

```
gaggatccga agacaggtgg tgctccgggc ggcgcaccgg gtggcgctcc gggcggtgcc        60
ccgggaggtg ctccgggtgg ggcgccaggc ggtgctccgg ctggagcgcc gggcggtgca       120
ccgggtgggg ctccgggtgg cgcaccgggc ggtgcgccag gaagtcttcg gatccag         177
```

```
<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence:synthetic

<400> SEQUENCE: 8

Met Gly Lys Gly Lys Ala Pro Gly Lys Ala Val
 1               5                  10
```

```
<210> SEQ ID NO 9
<211> LENGTH: 44
<212> TYPE: DNA
<213> ORGANISM: Artificial Sequence
<220> FEATURE:
<223> OTHER INFORMATION: Description of Artificial Sequence:synthetic

<400> SEQUENCE: 9
gaggatccag accatgggta aaggaaaagc accgggtaaa gcgc                         44
```

```
<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence:synthetic

<400> SEQUENCE: 10

Val Gly Val Pro
 1
```

```
<210> SEQ ID NO 11
<211> LENGTH: 48
<212> TYPE: DNA
<213> ORGANISM: Artificial Sequence
<220> FEATURE:
<223> OTHER INFORMATION: Description of Artificial Sequence:synthetic

<400> SEQUENCE: 11
ctcctaggtc tggtacccat ttccttttcg tggcccattt cgcggtcc                     48
```

```
<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence:synthetic

<400> SEQUENCE: 12

Met Gly Lys Gly Lys Ala Pro Gly Lys Ala Pro
 1               5                  10
```

```
<210> SEQ ID NO 13
<211> LENGTH: 39
<212> TYPE: DNA
<213> ORGANISM: Artificial Sequence
<220> FEATURE:
<223> OTHER INFORMATION: Description of Artificial Sequence:synthetic

<400> SEQUENCE: 13
gaggatccat gggtaaagga aaagcaccgg gtaaagcgc                               39
```

```
<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence:synthetic

<400> SEQUENCE: 14

Gly Gly Ala Pro
  1

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence:synthetic

<400> SEQUENCE: 15
ttggtgttcc gtaagcttga attcggatcc ag                                    32

<210> SEQ ID NO 16
<211> LENGTH: 5
<212> TYPE: PRT
<213> ORGANISM: Artificial Sequence
<220> FEATURE:
<221> NAME/KEY: VARIANT
<222> LOCATION: (1)..(5)
<223> OTHER INFORMATION: Description of Artificial Sequence:synthetic;
      residues at positions 1, 3, 5 can vary; residue 1
      is Phe, Leu, Ile, Val, Tyr or Trp; residue 3 is
      Ala or Gly; residue 5 is Phe, Leu, Ile, Met, Ala
      or Val

<400> SEQUENCE: 16

Xaa Pro Xaa Xaa Gly
  1               5

<210> SEQ ID NO 17
<211> LENGTH: 4
<212> TYPE: PRT
<213> ORGANISM: Artificial Sequence
<220> FEATURE:
<221> NAME/KEY: VARIANT
<222> LOCATION: (1)..(4)
<223> OTHER INFORMATION: Description of Artificial Sequence:synthetic;
      residue at position 1 can vary and is Phe, Leu,
      Ile, Val, Tyr or Trp

<400> SEQUENCE: 17

Xaa Pro Gly Gly
  1

<210> SEQ ID NO 18
<211> LENGTH: 160
<212> TYPE: PRT
<213> ORGANISM: Artificial Sequence
<220> FEATURE:
<223> OTHER INFORMATION: Description of Artificial Sequence:synthetic

<400> SEQUENCE: 18

Gly Gly Ala Pro Gly Gly Ala Pro Gly Gly Ala Pro Gly Gly Ala Pro
  1               5                  10                  15

Gly Gly Ala Pro Gly Gly Ala Pro Gly Gly Ala Pro Gly Gly Ala Pro
             20                  25                  30

Gly Gly Ala Pro Gly Gly Ala Pro Gly Gly Ala Pro Gly Gly Ala Pro
         35                  40                  45
```

```
Gly Gly Ala Pro Gly Gly Ala Pro Gly Gly Ala Pro Gly Gly Ala Pro
        50                  55                  60

Gly Gly Ala Pro Gly Gly Ala Pro Gly Gly Ala Pro Gly Gly Ala Pro
 65                  70                  75                  80

Gly Gly Ala Pro Gly Gly Ala Pro Gly Gly Ala Pro Gly Gly Ala Pro
                     85                  90                  95

Gly Gly Ala Pro Gly Gly Ala Pro Gly Gly Ala Pro Gly Gly Ala Pro
            100                 105                 110

Gly Gly Ala Pro Gly Gly Ala Pro Gly Gly Ala Pro Gly Gly Ala Pro
        115                 120                 125

Gly Gly Ala Pro Gly Gly Ala Pro Gly Gly Ala Pro Gly Gly Ala Pro
 130                 135                 140

Gly Gly Ala Pro Gly Gly Ala Pro Gly Gly Ala Pro Gly Gly Ala Pro
145                 150                 155                 160
```

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence:synthetic

<400> SEQUENCE: 19

```
Gly Arg Gly Asp Ser Pro
 1               5
```

<210> SEQ ID NO 20
<211> LENGTH: 11
<212> TYPE: DNA
<213> ORGANISM: Artificial Sequence
<220> FEATURE:
<223> OTHER INFORMATION: Description of Artificial Sequence:synthetic

<400> SEQUENCE: 20
ccaggcgttg g                                                          11

<210> SEQ ID NO 21
<211> LENGTH: 20
<212> TYPE: PRT
<213> ORGANISM: Artificial Sequence
<220> FEATURE:
<223> OTHER INFORMATION: Description of Artificial Sequence:synthetic

<400> SEQUENCE: 21

```
Met Arg Gly Ser His His His His His His Gly Ile Gln Tyr Met Gly
 1               5                  10                  15

Val Gly Val Pro
            20
```

<210> SEQ ID NO 22
<211> LENGTH: 15
<212> TYPE: DNA
<213> ORGANISM: Artificial Sequence
<220> FEATURE:
<221> NAME/KEY: variation
<222> LOCATION: (1)..(15)
<223> OTHER INFORMATION: Description of Artificial Sequence:synthetic;
      nucleotides at positions 3, 6, 9, 12 and 15 can
      vary and can be g, a, t or c

<400> SEQUENCE: 22
ccngcngtng gngtn                                                      15

<210> SEQ ID NO 23
<211> LENGTH: 15
<212> TYPE: DNA
<213> ORGANISM: Artificial Sequence
<220> FEATURE:
<221> NAME/KEY: variation
<222> LOCATION: (1)..(15)
<223> OTHER INFORMATION: Description of Artificial Sequence:synthetic;
      nucleotides at positions 2, 5, 8, 11 and 14 can
      vary and can be g, a, t or c

<400> SEQUENCE: 23
cnggnacncc nacng                                                      15

<210> SEQ ID NO 24
<211> LENGTH: 11
<212> TYPE: DNA
<213> ORGANISM: Artificial Sequence
<220> FEATURE:
<223> OTHER INFORMATION: Description of Artificial Sequence:synthetic

<400> SEQUENCE: 24
tcgagccatg g                                                          11

<210> SEQ ID NO 25
<211> LENGTH: 11
<212> TYPE: DNA
<213> ORGANISM: Artificial Sequence
<220> FEATURE:
<221> NAME/KEY: variation
<222> LOCATION: (1)..(11)
<223> OTHER INFORMATION: Description of Artificial Sequence:synthetic;
      nucleotides at positions 4, 5, 6, 7  and 8 can
      vary and can be g, a, t or c

<400> SEQUENCE: 25
ccannnnntg g                                                          11

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence:synthetic

<400> SEQUENCE: 26
cgggatccag gcgttggt                                                   18

<210> SEQ ID NO 27
<211> LENGTH: 17
<212> TYPE: DNA
<213> ORGANISM: Artificial Sequence
<220> FEATURE:
<223> OTHER INFORMATION: Description of Artificial Sequence:synthetic

<400> SEQUENCE: 27
ccaggcgttg gatcccg                                                    17

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence:synthetic

<400> SEQUENCE: 28
tcggatccag accatgggcg tt                                              22

<210> SEQ ID NO 29
<211> LENGTH: 36
<212> TYPE: DNA
<213> ORGANISM: Artificial Sequence
<220> FEATURE:
<223> OTHER INFORMATION: Description of Artificial Sequence:synthetic

<400> SEQUENCE: 29
ggcgttggtg taccgtaagc ttgaattcgg atccag                                36

<210> SEQ ID NO 30
<211> LENGTH: 100
<212> TYPE: PRT
<213> ORGANISM: Artificial Sequence
<220> FEATURE:
<223> OTHER INFORMATION: Description of Artificial Sequence:synthetic

<400> SEQUENCE: 30

Gly Val Pro Gly Val Gly Val Pro Gly Val Gly Val Pro Gly Val Gly
 1               5                  10                  15

Val Pro Gly Val Gly Val Pro Gly Val Gly Val Pro Gly Val Gly Val
                20                  25                  30

Pro Gly Val Gly Val Pro Gly Val Gly Val Pro Gly Val Gly Val Pro
            35                  40                  45

Gly Val Gly Val Pro Gly Val Gly Val Pro Gly Val Gly Val Pro Gly
        50                  55                  60

Val Gly Val Pro Gly Val Gly Val Pro Gly Val Gly Val Pro Gly Val
 65                  70                  75                  80

Gly Val Pro Gly Val Gly Val Pro Gly Val Gly Val Pro Gly Val Gly
                85                  90                  95

Val Pro Gly Val
            100

<210> SEQ ID NO 31
<211> LENGTH: 43
<212> TYPE: PRT
<213> ORGANISM: Artificial Sequence
<220> FEATURE:
<223> OTHER INFORMATION: Description of Artificial Sequence:synthetic

<400> SEQUENCE: 31

Gly Gly Ala Pro Gly Gly Ala Pro Gly Gly Ala Pro Gly Gly Ala Pro
 1               5                  10                  15

Gly Gly Ala Pro Gly Gly Ala Pro Gly Gly Ala Pro Gly Gly Ala Pro
                20                  25                  30

Gly Gly Ala Pro Gly Gly Ala Pro Gly Gly Ala
            35                  40

<210> SEQ ID NO 32
<211> LENGTH: 43
<212> TYPE: PRT
<213> ORGANISM: Artificial Sequence
<220> FEATURE:
<223> OTHER INFORMATION: Description of Artificial Sequence:synthetic

<400> SEQUENCE: 32

Gly Gly Ala Pro Gly Gly Ala Pro Gly Gly Ala Pro Gly Gly Ala Pro
 1               5                  10                  15

Gly Gly Ala Pro Gly Gly Ala Pro Gly Gly Ala Pro Gly Gly Ala Pro
                20                  25                  30

Gly Gly Ala Pro Gly Gly Ala Pro Gly Gly Ala
            35                  40

```
<210> SEQ ID NO 33
<211> LENGTH: 43
<212> TYPE: PRT
<213> ORGANISM: Artificial Sequence
<220> FEATURE:
<223> OTHER INFORMATION: Description of Artificial Sequence:synthetic

<400> SEQUENCE: 33

Gly Gly Ala Pro Gly Gly Ala Pro Gly Gly Ala Pro Gly Gly Ala Pro
 1               5                  10                  15

Gly Gly Ala Pro Gly Gly Ala Pro Gly Gly Ala Pro Gly Gly Ala Pro
             20                  25                  30

Gly Gly Ala Pro Gly Gly Ala Pro Gly Gly Ala
         35                  40

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence:synthetic

<400> SEQUENCE: 34

Ala Val Gly Val Pro
 1               5

<210> SEQ ID NO 35
<211> LENGTH: 50
<212> TYPE: PRT
<213> ORGANISM: Artificial Sequence
<220> FEATURE:
<223> OTHER INFORMATION: Description of Artificial Sequence:synthetic

<400> SEQUENCE: 35

Ala Val Gly Val Pro Ala Val Gly Val Pro Ala Val Gly Val Pro Ala
 1               5                  10                  15

Val Gly Val Pro Ala Val Gly Val Pro Ala Val Gly Val Pro Ala Val
             20                  25                  30

Gly Val Pro Ala Val Gly Val Pro Ala Val Gly Val Pro Ala Val Gly
         35                  40                  45

Val Pro
     50

<210> SEQ ID NO 36
<211> LENGTH: 43
<212> TYPE: DNA
<213> ORGANISM: Artificial Sequence
<220> FEATURE:
<223> OTHER INFORMATION: Description of Artificial Sequence:synthetic

<400> SEQUENCE: 36
ctcctaggta cccatttcct tttcgtggcc catttcgcgg tcc                      43

<210> SEQ ID NO 37
<211> LENGTH: 35
<212> TYPE: DNA
<213> ORGANISM: Artificial Sequence
<220> FEATURE:
<223> OTHER INFORMATION: Description of Artificial Sequence:synthetic

<400> SEQUENCE: 37
gacaaccaca aggcattcga acttaagcct aggtc                               35

<210> SEQ ID NO 38
```

```
<211> LENGTH: 35
<212> TYPE: DNA
<213> ORGANISM: Artificial Sequence
<220> FEATURE:
<223> OTHER INFORMATION: Description of Artificial Sequence:synthetic

<400> SEQUENCE: 38
caggtggtgc tccgtaagct tgaattcgga tccag                                35

<210> SEQ ID NO 39
<211> LENGTH: 31
<212> TYPE: DNA
<213> ORGANISM: Artificial Sequence
<220> FEATURE:
<223> OTHER INFORMATION: Description of Artificial Sequence:synthetic

<400> SEQUENCE: 39
accacgaggc attcgaactt aagcctaggt c                                    31

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence:synthetic

<400> SEQUENCE: 40

Ala Pro Gly Val Gly Val
 1               5

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence:synthetic

<400> SEQUENCE: 41

Gly Val Gly Val Pro
 1               5

<210> SEQ ID NO 42
<211> LENGTH: 600
<212> TYPE: PRT
<213> ORGANISM: Artificial Sequence
<220> FEATURE:
<223> OTHER INFORMATION: Description of Artificial Sequence:synthetic

<400> SEQUENCE: 42

Gly Val Gly Val Pro Gly Val Gly Val Pro Gly Val Gly Val Pro Gly
 1               5                  10                  15

Val Gly Val Pro Gly Val Gly Val Pro Gly Val Gly Val Pro Gly Val
                20                  25                  30

Gly Val Pro Gly Val Gly Val Pro Gly Val Gly Val Pro Gly Val Gly
            35                  40                  45

Val Pro Gly Val Gly Val Pro Gly Val Gly Val Pro Gly Val Gly Val
        50                  55                  60

Pro Gly Val Gly Val Pro Gly Val Gly Val Pro Gly Val Gly Val Pro
 65                  70                  75                  80

Gly Val Gly Val Pro Gly Val Gly Val Pro Gly Val Gly Val Pro Gly
                85                  90                  95

Val Gly Val Pro Gly Val Gly Val Pro Gly Val Gly Val Pro Gly Val
                100                 105                 110

Gly Val Pro Gly Val Gly Val Pro Gly Val Gly Val Pro Gly Val Gly
```

-continued

```
            115                 120                 125
Val Pro Gly Val Gly Val Pro Gly Val Gly Val Pro Gly Val Gly Val
    130                 135                 140
Pro Gly Val Gly Val Pro Gly Val Gly Val Pro Gly Val Gly Val Pro
145                 150                 155                 160
Gly Val Gly Val Pro Gly Val Gly Val Pro Gly Val Gly Val Pro Gly
                165                 170                 175
Val Gly Val Pro Gly Val Gly Val Pro Gly Val Gly Val Pro Gly Val
            180                 185                 190
Gly Val Pro Gly Val Gly Val Pro Gly Val Gly Val Pro Gly Val Gly
        195                 200                 205
Val Pro Gly Val Gly Val Pro Gly Val Gly Val Pro Gly Val Gly Val
    210                 215                 220
Pro Gly Val Gly Val Pro Gly Val Gly Val Pro Gly Val Gly Val Pro
225                 230                 235                 240
Gly Val Gly Val Pro Gly Val Gly Val Pro Gly Val Gly Val Pro Gly
                245                 250                 255
Val Gly Val Pro Gly Val Gly Val Pro Gly Val Gly Val Pro Gly Val
            260                 265                 270
Gly Val Pro Gly Val Gly Val Pro Gly Val Gly Val Pro Gly Val Gly
        275                 280                 285
Val Pro Gly Val Gly Val Pro Gly Val Gly Val Pro Gly Val Gly Val
    290                 295                 300
Pro Gly Val Gly Val Pro Gly Val Gly Val Pro Gly Val Gly Val Pro
305                 310                 315                 320
Gly Val Gly Val Pro Gly Val Gly Val Pro Gly Val Gly Val Pro Gly
                325                 330                 335
Val Gly Val Pro Gly Val Gly Val Pro Gly Val Gly Val Pro Gly Val
            340                 345                 350
Gly Val Pro Gly Val Gly Val Pro Gly Val Gly Val Pro Gly Val Gly
        355                 360                 365
Val Pro Gly Val Gly Val Pro Gly Val Gly Val Pro Gly Val Gly Val
    370                 375                 380
Pro Gly Val Gly Val Pro Gly Val Gly Val Pro Gly Val Gly Val Pro
385                 390                 395                 400
Gly Val Gly Val Pro Gly Val Gly Val Pro Gly Val Gly Val Pro Gly
                405                 410                 415
Val Gly Val Pro Gly Val Gly Val Pro Gly Val Gly Val Pro Gly Val
            420                 425                 430
Gly Val Pro Gly Val Gly Val Pro Gly Val Gly Val Pro Gly Val Gly
        435                 440                 445
Val Pro Gly Val Gly Val Pro Gly Val Gly Val Pro Gly Val Gly Val
    450                 455                 460
Pro Gly Val Gly Val Pro Gly Val Gly Val Pro Gly Val Gly Val Pro
465                 470                 475                 480
Gly Val Gly Val Pro Gly Val Gly Val Pro Gly Val Gly Val Pro Gly
                485                 490                 495
Val Gly Val Pro Gly Val Gly Val Pro Gly Val Gly Val Pro Gly Val
            500                 505                 510
Gly Val Pro Gly Val Gly Val Pro Gly Val Gly Val Pro Gly Val Gly
        515                 520                 525
Val Pro Gly Val Gly Val Pro Gly Val Gly Val Pro Gly Val Gly Val
    530                 535                 540
```

```
Pro Gly Val Gly Val Pro Gly Val Gly Val Pro Gly Val Gly Val Pro
545                 550                 555                 560

Gly Val Gly Val Pro Gly Val Gly Val Pro Gly Val Gly Val Pro Gly
                565                 570                 575

Val Gly Val Pro Gly Val Gly Val Pro Gly Val Gly Val Pro Gly Val
            580                 585                 590

Gly Val Pro Gly Val Gly Val Pro
        595                 600

<210> SEQ ID NO 43
<211> LENGTH: 50
<212> TYPE: PRT
<213> ORGANISM: Artificial Sequence
<220> FEATURE:
<223> OTHER INFORMATION: Description of Artificial Sequence:synthetic

<400> SEQUENCE: 43

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
            20                  25                  30

Gly Val Pro Gly Val Gly Val Pro Gly Val Gly Val Pro Gly Val Gly
        35                  40                  45

Val Pro
    50

<210> SEQ ID NO 44
<211> LENGTH: 7
<212> TYPE: DNA
<213> ORGANISM: Artificial Sequence
<220> FEATURE:
<223> OTHER INFORMATION: Description of Artificial Sequence:synthetic

<400> SEQUENCE: 44 ccatggc                                                                  7

<210> SEQ ID NO 45
<211> LENGTH: 48
<212> TYPE: PRT
<213> ORGANISM: Artificial Sequence
<220> FEATURE:
<223> OTHER INFORMATION: Description of Artificial Sequence:synthetic

<400> SEQUENCE: 45

Gly Gly Ala Pro Gly Gly Ala Pro Gly Gly Ala Pro Gly Gly Ala Pro
1               5                   10                  15

Gly Gly Ala Pro Gly Gly Ala Pro Gly Gly Ala Pro Gly Gly Ala Pro
            20                  25                  30

Gly Gly Ala Pro Gly Gly Ala Pro Gly Gly Ala Pro Gly Gly Ala Pro
        35                  40                  45

<210> SEQ ID NO 46
<211> LENGTH: 5
<212> TYPE: DNA
<213> ORGANISM: Artificial Sequence
<220> FEATURE:
<223> OTHER INFORMATION: Description of Artificial Sequence:synthetic

<400> SEQUENCE: 46 ttggt                                                                    5

<210> SEQ ID NO 47
<211> LENGTH: 7
```

```
<212> TYPE: DNA
<213> ORGANISM: Artificial Sequence
<220> FEATURE:
<223> OTHER INFORMATION: Description of Artificial Sequence:synthetic

<400> SEQUENCE: 47 ccaggcg                                                                  7

<210> SEQ ID NO 48
<211> LENGTH: 8
<212> TYPE: DNA
<213> ORGANISM: Artificial Sequence
<220> FEATURE:
<223> OTHER INFORMATION: Description of Artificial Sequence:synthetic

<400> SEQUENCE: 48 cgcaacca                                                                 8

<210> SEQ ID NO 49
<211> LENGTH: 4
<212> TYPE: DNA
<213> ORGANISM: Artificial Sequence
<220> FEATURE:
<223> OTHER INFORMATION: Description of Artificial Sequence:synthetic

<400> SEQUENCE: 49 ggtc                                                                     4

<210> SEQ ID NO 50
<211> LENGTH: 6
<212> TYPE: DNA
<213> ORGANISM: Artificial Sequence
<220> FEATURE:
<223> OTHER INFORMATION: Description of Artificial Sequence:synthetic

<400> SEQUENCE: 50 ggatcc                                                                   6
```

HYPEREXPRESSION OF BIOELASTIC POLYPEPTIDES

CROSS REFERENCES

This application is a continuation application of U.S. patent application Ser. No. 08/423,642, filed Apr. 14, 1995 now abandoned.

This invention was made with Government support under Contract No. DAAK60-93-C-0094 awarded by the Department of the Army. The Government has certain rights in the invention.

INTRODUCTION

1. Technical Field

The present invention relates to the production of biocompatible structural polymers.

2. Background

Global environmental concerns resulting in ever-mounting costs for disposal of solid waste, in addition to the toxic and hazardous chemicals required in petroleum-based polymer production, have increased demand for polymers which are biodegradable and of benign production. Because petroleum is an exhaustible resource, there is a pressing need to decrease dependence on petroleum-based products. Protein-based polymers provide a promising answer to these problems as they are biodegradable, they can be produced from renewable resources, and their processing can be water based not requiring noxious chemicals. A particularly favorable subset of protein-based polymers are those which exhibit inverse temperature transitional behavior. As a key step in biodegradation, these polymers can be designed to have half-lives ranging from days to decades.

Protein-based polymers offer a range of materials similar to that of oil-based polymers. For example, they can be hydrogels, elastomers, and plastics. The elastic and plastic protein-based polymers exhibit elastic moduli that can range from $10^4$ to $10^5$ dynes/cm$^2$ for the hydrogels, to $10^6$ to $10^8$ dynes/cm$^2$ for the elastomers, and to $10^9$ dynes/cm$^2$ or greater for the plastics which are cross-linked matrices above a certain critical temperature (D. W. Urry, J. Jaggard, K. U. Prasad, T. Parker, R. D. Harris (1991) in *Biotechnology and Polymers*, C. G. Gebelein, ed. (Plenum Press, New York) pp. 265–274.) Because the plastic protein-based materials are elastic below their critical temperature, these materials are collectively called bioelastic materials. They can be designed to catalyze free energy transduction involving the variables of mechanical force, temperature, pressure, chemical potential, electrochemical potential, and electromagnetic radiation; they can be biodegradable with chemical clocks to set their half-lives, such that they can be environmentally friendly over their complete life, during their production and disposal.

Bioelastomeric polypeptides are a relatively new development that arose in the laboratories of one of the present inventors and are disclosed in a series of previously filed patents and patent applications. For example, U.S. Pat. No. 4,474,851 describes a number of tetrapeptide and pentapeptide repeating units that can be used to form a bioelastic polymer. Specific bioelastic polymers are also described in U.S. Pat. Nos. 4,132,746, 4,187,852, 4,589,882, and 4,870,055. U.S. Pat. No. 5,064,430 describes polynonapeptide bioelastomers. Bioelastic polymers are also disclosed in related patents: U.S. Pat. Nos. 4,605,413, 4,976,734, and 4,693,718, entitled "Stimulation of Chemotaxis by Chemotactic Peptides"; U.S. Pat. No. 4,898,926, entitled "Bioelastomer Containing Tetra/Pentapeptide Units"; U.S. Pat. No. 4,783,523 entitled "Temperature Correlated Force and Structure Development of Elastin Polytetrapeptide"; U.S. Pat. Nos. 5,032,271, 5,085,055, and 5,255,518, entitled "Reversible Mechanochemical Engines Comprised of Bioelastomers Capable of Modulable Temperature Transitions for the Interconversion of Chemical and Mechanical Work"; U.S. Pat. No. 4,500,700, entitled "Elastomeric Composite Material Comprising a Polypeptide"; U.S. Pat. No. 5,250,516 entitled "Bioelastomeric Materials Suitable for the Protection of Wound Repair Sites"; and U.S. Pat. No. 5,336,256 entitled "Elastomeric Polypeptides as Vascular Prosthetic Materials." A number of other bioelastic materials and methods for their use are described in pending U.S. patent applications including: U.S. Ser. No. 07/962,608, filed Oct. 16, 1992, entitled "Bioelastomeric Drug Delivery System"; U.S. Ser. No. 08/187,441, filed Jan. 24, 1994, entitled "Photoresponsive Polymers"; and U.S. Ser. No. 08/246,874, filed May 20, 1994, entitled "Elastomeric Polypeptide Matrices for Preventing Adhesion of Biological Materials". All of these patents and patent applications are herein incorporated by reference, as they describe in detail bioelastomers and/or components thereof and their preparation. This information can be used in preparing bioelastic polymers using the compositions and methods of the present invention.

The bioelastomers were developed based on investigations into the natural bioelastomer elastin. Elastin is comprised of a single protein containing a serial alignment of alanine-rich, lysine-containing cross-linking sequences alternating with glycine-rich hydrophobic sequences. With the entire bovine sequence known, the most striking hydrophobic sequences, both from the standpoint of length and of composition, are one that contains a polypentapeptide (PPP) and one that contains a polyhexapeptide (PHP). Elastin also contains several tetrapeptide (TP) units. As a result of work conducted by one of the present inventors, the polypentapeptide of elastin when cross-linked has been found to be elastomeric and the polyhexapeptide thereof has been found to be non-elastomeric and appears to provide a means for aligning and interlocking the chains during elastogenesis. It has also been found that the elastin polypentapeptide and polytetrapeptide are both conformation-based elastomers that develop entropic elasticity and strength on undergoing an inverse temperature transition to form a regular β-turn containing dynamic structure.

A typical biological elastic fiber is comprised of a large elastin core covered with a fine surface layer of microfibrillar protein. Elastin is formed upon cross-linking of the lysine residues of tropoelastin. The repeating elastin pentapeptide has the formula (VPGVG)$_n$ (SEQ ID NO:1), while the repeating hexapeptide has the formula (VAPGVG)$_n$ (SEQ ID NO:2), where n varies depending upon the species (H. Yeh, et al. (1987) *Collagen and Related Research* 7:235). The tetrapeptide unit has the formula (VPGG) (SEQ ID NO:3). These sequences, of course, utilize the standard one-letter abbreviation for the constituent amino acids. In a most striking example the sequence (VPGVG)$_n$ (SEQ ID NO:1), occurs in bovine elastin with n=11 without a single substitution (H. Yeh, et al. (1987)).

Bioelastic materials are based on elastomeric and related polypeptides comprised of repeating peptide sequences (D. W. Urry (1993a) *Angew. Chem.* (German) 105:859; *Angew. Chem. Omt. Ed. Engl.* 32:819); they may also be called elastic and plastic protein-based polymers. It has been found that these polypeptides are soluble in water below 25° C. but on raising the temperature they associate reversibly to form a water-containing viscoelastic phase in the polypentapeptide (PPP) and polytetrapeptide (PTP) cases, whereas in the polyhexapeptide (PHP) case, they associate irreversibly in water to form a granular precipitate, which usually requires the addition of trifluoroethanol to the aggregate for redissolution. On cross-linking, the PPP and PTP have been found to be elastomers, whereas PHP is not elastomeric. A particularly interesting analog of the naturally occurring sequences is poly(VPAVG) (SEQ ID NO:4) or equivalently poly(AVGVP) (SEQ ID NO:34) as it reversibly forms a plastic on raising the temperature.

For purposes of clarification, it is noted that the reversible temperature elicited aggregation, which gives rise upon standing to a dense viscoelastic phase, is called coacervation. The viscoelastic phase is called the coacervate, and the solution above the coacervate is referred to as the equilibrium solution.

Most importantly, cross-Linked PPP, PTP and analogs thereof at fixed length exhibit elastomeric force development at different temperatures spanning a range of up to about 75° C. depending upon several controllable variables. Moreover, these cross-linked elastomers develop near maximum elastomeric force over a relatively narrow temperature range. Thus, by synthesizing bioelastomeric materials having varying molar amounts of the constituent pentamers and tetramers together with such units modified by hexameric repeating units, and by choosing a particular solvent to support the initial viscoelastic phase, it is possible to rigorously control the temperature at which the obtained bioelastomer develops elastomeric force.

In general, the process of raising the temperature to form the above elastomeric state is an inverse temperature transition resulting in the development of a regular non-random structure, unlike typical rubbers, which utilizes, as a characteristic component, hydrophobic intramolecular interactions. The regular structure is proposed to be a β-spiral, a loose water-containing helical structure with β-turns as spacers between turns of the helix which provides hydrophobic contacts between helical turns and has suspended peptide segments between β-turns. These peptide segments are free to undergo large amplitude, low frequency rocking motions called librations. This mechanism of elasticity is called the librational entropy mechanism of elasticity (or is sometimes referred to as resulting from damping of internal chain dynamics on extension). The elastomeric force of these various bioelastomers develops as the regular structure thereof develops. Further, a loss of regular structure by high temperature denaturation results in loss of elastomeric force. These polymers can be prepared with widely different water compositions, with a wide range of hydrophobicities, with almost any desired shape and porosity, and with a variable degree of cross-linking by selecting different amino acids for the different positions of the monomeric units and by varying the cross-linking process, e.g. chemical, photochemical, enzymatic, irradiative, used to form the final product. The bioelastic material can be made available in different physical forms, such as sheets, gels, foams, or powders. The polymer can be present as a copolymer containing a mixture of tetrameric and pentameric units and further can contain other monomeric units.

Bioelastic materials have been proposed for a number of uses and apparatuses, as indicated by the general subject matter of the applications and patents set forth above. On the non-medical side, there are transducers, molecular machines, superabsorbents, biodegradable plastics, and compositions for controlled release of agricultural crop enhancement agents, such as herbicides, pesticides, growth factors and fertilizers. The bioelastic compositions and machines respond to pressure, chemical, light, and/or thermal changes in the environment by phase transitions (e.g., viscosity or turbidity changes) or by contraction or relaxation to reversibly transduce these energies into mechanical work (for example, as described in U.S. Pat. No. 5,226,292). Compositions tested to date have been shown to be extraordinarily biocompatible, allowing for medical applications ranging from the prevention of post-surgical adhesions (D. W. Urry et al. (1993) *Biological Polymers: Medical, Pharmaceutical and Industrial Applications*, pp. 82–103) and tissue reconstruction to programmed drug delivery. Materials functioning as insulator materials for isolating wound repair sites from adhesions for the protection of burn areas, and to facilitate repair of the damaged tissue have been described in U.S. Pat. No. 5,250,516 and U.S. patent application Ser. No. 08/246,874, filed May 20, 1994.

Bioproduction of these polymers has been estimated to be competitive with production of petroleum-based polymers for many applications. Expression of a small elastic protein based polymer as a fusion protein in *E. coli* has been previously demonstrated (D. T. McPherson, et al. (1992) *Biotechnol. Frog.* 8:347). This publication, a publication arising from the laboratory of one of the present inventors, describes the production and purification of a recombinant elastomeric polypeptide, G-(VPGVG)$_{19}$-VPGV (SEQ ID NO:30), from *Escherichia coli*. The described method relies on an expensive inducer, IPTG, for gene expression, and an expensive protease, factor Xa, for cleavage of the polypentapeptide away from the glutathione S-transferase carrier protein. A more cost effective manner for expressing bioelastmers would be advantageous. There remains a need for the expression of synthetic polymer genes in large quantities, and to prepare polymers of varied design and exact composition without employing hazardous and noxious solvents and chemicals.

RELEVANT LITERATURE

1. D. W. Urry, J. Jaggard, K. U. Prasad, T. Parker, R. D. Harris (1991) in *Biotechnology and Polymers*, C. G. Gebelein, ed. (Plenum Press, New York) pp. 265–274.
2. D. W. Urry et al. (1993) *Biological Polymers: Medical, Pharmaceutical and Industrial Applications*, pp. 82–103.
3. D. W. Urry (1993a) *Angew. Chem.* (German) 105:859; *Angew. Chem. Omt. Ed. Engl.* 32:819.
4. H. Yeh, et al. (1987) *Collagen and Related Research* 7:235.
5. D. T. McPherson, et al. (1992) *Biotechnol. Prog.* 8:347.
6. F. W. Studier and B. A. Moffat (1986) *J. Mol. Biol.* 189:113.
7. U. K. Laemmli (1970) *Nature* 227:680.
8. C. Lee, A. Levin, and D. Branton (1987) *Anal. Biochem.* 166:308.
9. A. R. Spurr (1969) *Ultrastruct. Res.* 26:31.
10. K. D. Tartof and C. A. Hobbs (1987) *Bethesda Res. Lab. Focus* 9:12
11. J. Brosius (1984) *Gene* 27:161.
12. Y. Masui, T. Mizuno and M. Inouye (1984) *Bio/Technology* 2:81.
13. B. Lewin (1990) *Genes IV* (Oxford Univ. Press, New York) pp. 240.
14. H. Daniell, et al. (1994) in *Biochemical and Cellular Mechanisms of Stress Tolerance in Plants*, J. H. Cherry, Ed. (Springer-Verlag, New York) pp. 589–604.
15. D. C. Williams, R. M. Van Frank, W. L. Muth and J. P. Burnett (1982) *Science* 215:687.
16. E. G. Schoner, L. F. Ellis and B. E. Schoner (1985) *Bio/Technology* 3:151.

17. J. F. Kane and D. L. Hartley (1988) *Trends in Biotechnol.* 6:95.

18. M. Gribskov and R. R. Burgess (1983) *Gene* 26:109.

SUMMARY OF THE INVENTION

Accordingly, it is an object of the present invention to provide methods and compositions for synthesizing elastomeric materials in large quantities. It is a further object of the invention to provide cells expressing elastomeric materials.

According to the present invention, the foregoing and other objects are obtained by introducing into a host cell, a vector comprising a promoter operably linked to a nucleic acid encoding a bioelastic polypeptide comprising pentapeptide, tetrapeptide, hexapeptide or nonapeptide repeating units and growing the host cell to provide for expression of the polypeptide as at least 40% of the total cellular protein. The bioelastic polymer can optionally include non-bioelastic sequences ranging from single amino acid insertions to fusions with unrelated peptides. The fusion junction may be interrupted by a linker region providing for a cleavage site or merely reducing or eliminating steric hinderances between the bioelastomer and the peptide fused thereto. The bioelastic polymer can be expressed in prokaryotic systems, e.g., *Escherichia coli* or eukaryotic systems, e.g., yeast, plants or mammalian cells.

BRIEF DESCRIPTION OF THE DRAWINGS

The invention will be better understood by reference to the following detailed description of specific embodiments together with the figures that form part of this specification, wherein.

FIG. 3 Sequence of the $(GVGVP)_{10}$ (SEQ ID NO:43) gene (SEQ ID NO:5), comprising optimal codons for tobacco while maintaining maximal coding degeneracy.

FIGS. 5A and B Sequences of the $(AVGVP)_{10}$ (SEQ ID NO:35) gene and $(GGAP)_{12}$ (SEQ ID NO:45)gene.

FIGS. 6A and B Sequences of the AVGVP (SEQ ID NO:34) and GGAP (SEQ ID NO:8–15 and 36–39) adaptors.

DESCRIPTION OF SPECIFIC EMBODIMENTS

Figure 1B:
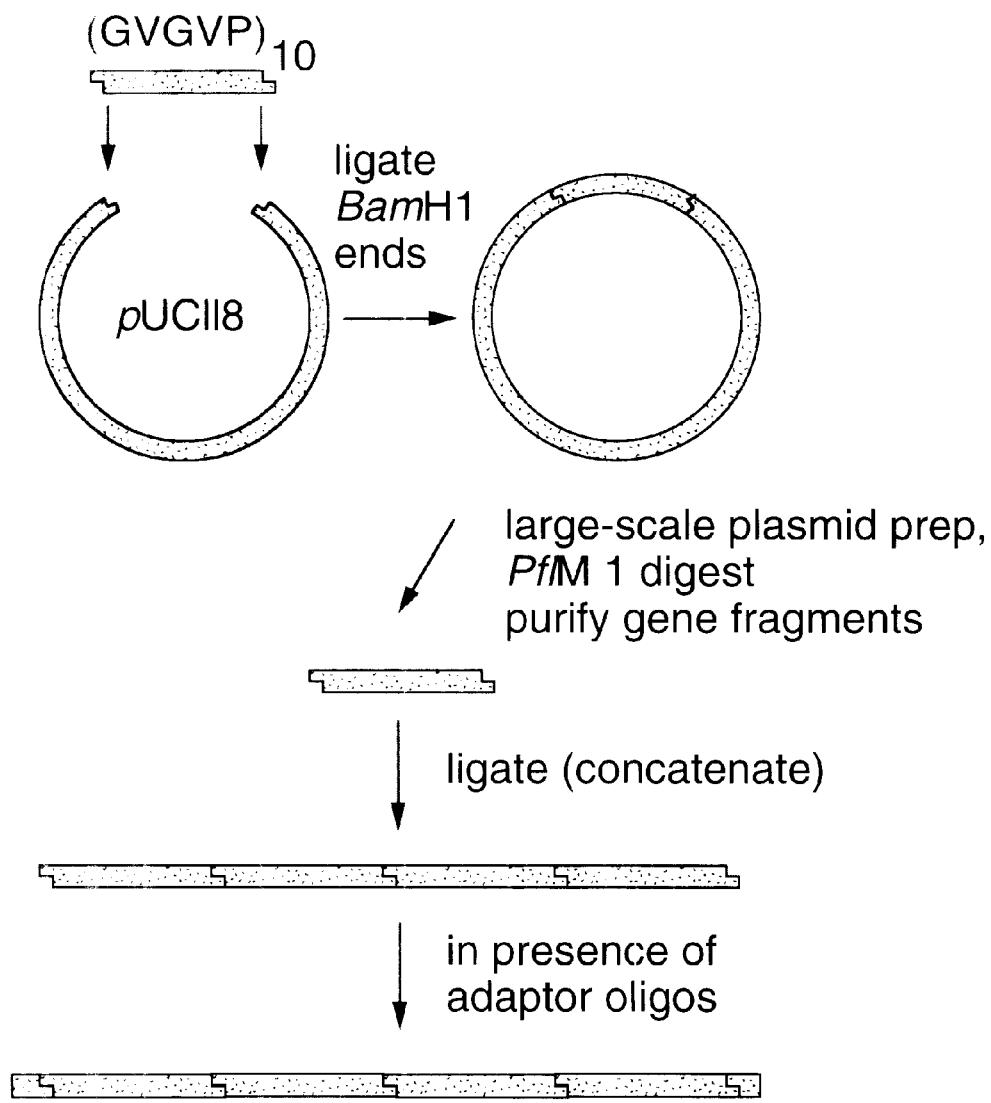
FIGS. 1A and B. Sequences of synthetic oligonucleotides (SEQ ID NOS:26–29 and SEQ ID NOS:46–49) used for the construction of $(GVGVP)_{120}$ (SEQ ID NO:42) using the 10 mer gene for $(GVGVP)_{10}$ to (SEQ ID NO:43). B. Scheme of cloning procedure.
Figure 2A:
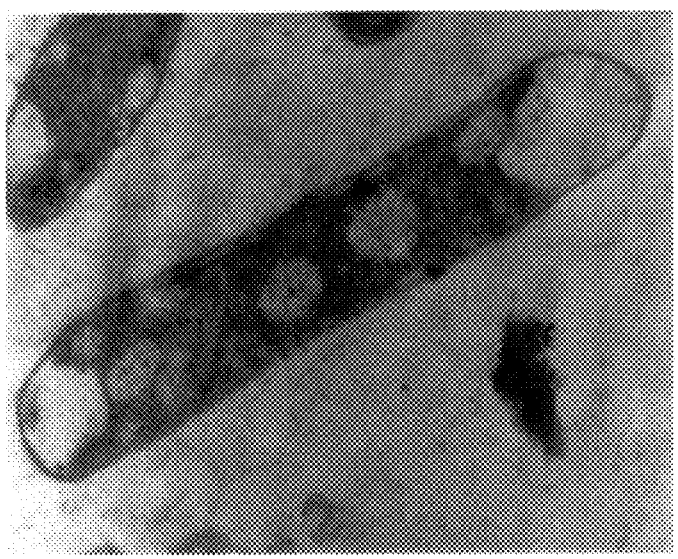
FIGS. 2A to F. Transmission Electron Micrographs of *E. coli* strain HMS 174 (DE3) transformed with pET 11d-120 mer (with the exception of F) showing polymer production at different durations of culture growth in uninduced and induced cells. A. Uninduced—6 hrs; B. Induced—6 hrs; C & E. Uninduced—24 hrs; D. Induced—24 hrs; F. Host strain without plasmid.
Figure 2B:
Figure 2C:
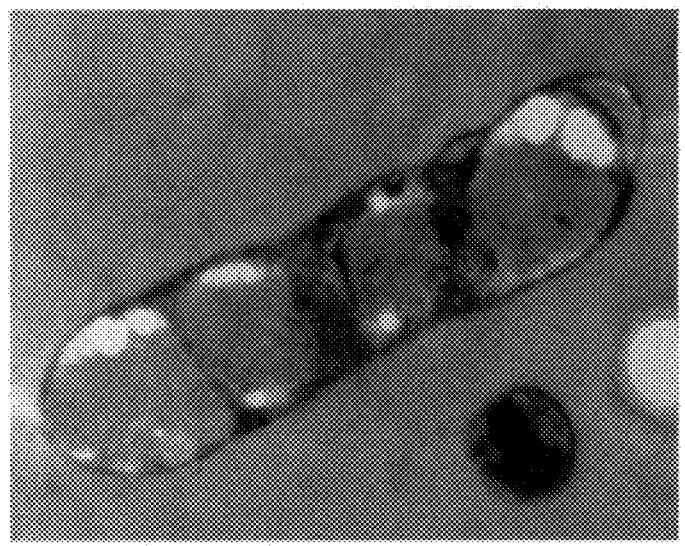
Figure 2D:
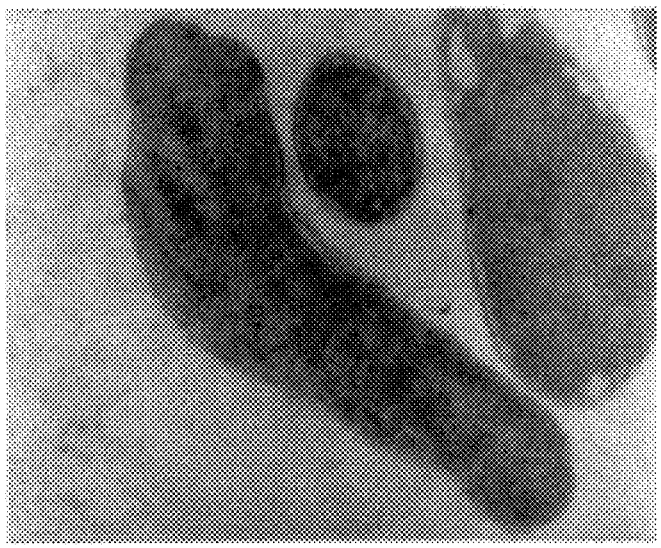
Figure 2E:
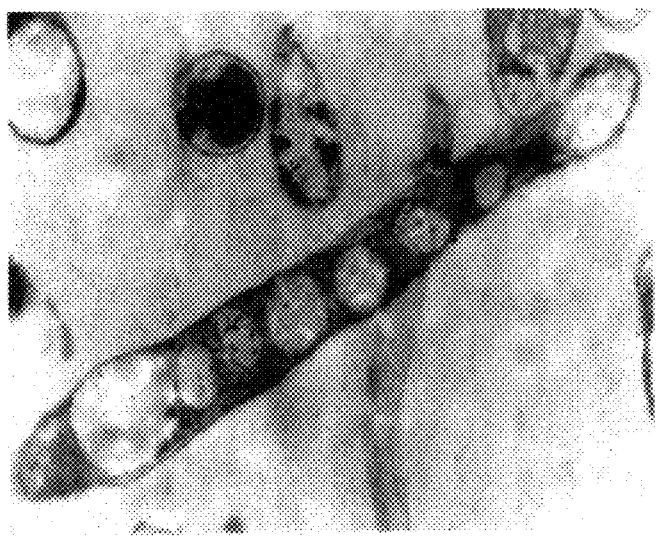
Figure 2F:
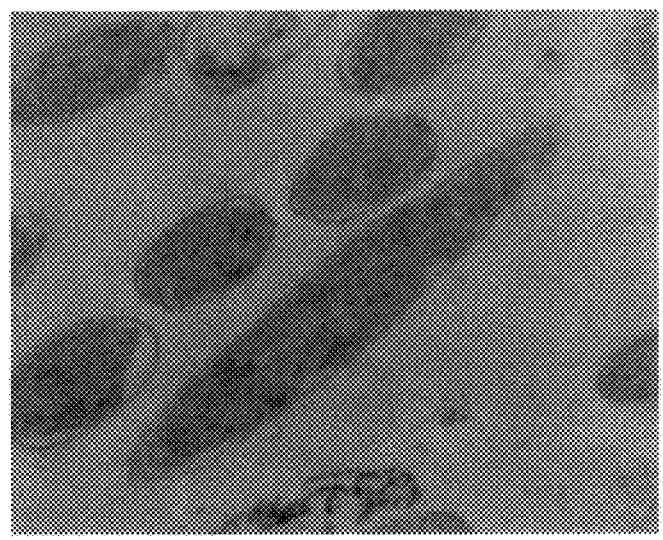

The method of the present invention can be used to produce bioelastic polymers that exhibit an inverse temperature transition. The term inverse temperature transition refers to the phase transition of certain polymers to a condensed state of greater order in water on raising the temperature through the transition temperature range, and the temperature at which the onset of this transition occurs is designated as the transition temperature ($T_t$) (Urry (1992); Urry (1993a) Angew. Chem., 105:859–883; Urry, D. W. (1993b) Angew. Chem. Int. Ed. Engl., 32:819–841). The temperature for this phase transition, commonly called coacervation, is determined by the hydrophobicity of the amino acids comprising the polymer. When more hydrophobic amino acids are included, the temperature is decreased, and when less hydrophobic amino acids are included, the temperature is increased. The dependence of the temperature range for the phase transition on the hydrophobicity of the composite amino acids provides the basis for a hydrophobicity scale dependent on the hydrophobic folding process of interest (See USSN 08/187,441 filed Jan. 24, 1994; Table 1). The hydrophobicity scale based thereon is called the $T_t$-based hydrophobicity scale and is useful in designing the bioelastic polymers. The phase transition can occur reversibly or irreversibly upon raising the temperature. For example, plastic β-spiral structures form irreversibly for poly(APGVGV), (SEQ ID NO:40) and reversibly for poly (VPAVG) (SEQ ID NO:16). The latter can exhibit elasticity below and through much of the transition temperature range but becomes a hard plastic once the transition is complete. Because of this, the material may be referred to as an inverse thermoplastic. Using the relative hydrophobicities of the amino acid side chains, it is possible to construct polymers which will exhibit inverse temperature transitions by a systematic, knowledge-based approach.

The temperature at which folding and assembly occur can be changed by altering a number of intrinsic or extrinsic factors. Intrinsic to a class of model proteins of 50,000 Da molecular weight or greater are: (a) the concentration of polymer itself, (b) changes in the amino acid composition within the bioelastic unit, (c) changes in the degree of ionization of functional side chains controlled by changes in pH, (d) the phosphorylation of side chains such as serine by enzymes called kinases, (e) the oxidation or reduction electrically, chemically or enzymatically of a side chain attached to the polymer, (f) photochemical reactions of attached chromophores and (g) chemical reactions of side chains in response to electromagnetic radiation. Extrinsic chemical changes affecting $T_t$ include the effects of salts, organic solutes and pressure. U.S. Pat. No. 5,226,292 from the laboratory of one of the present inventors details pressure-related effects. In addition there is a chain length dependence that becomes significant at lower molecular weights where shorter chain lengths result in higher values of $T_t$.

The structure of bioelastomers are described in detail in various patents and patent applications listed above which arose from the laboratories of one of the present inventors. A bioelastic material comprises either tetrapeptide, pentapeptide or nonapeptide monomers that individually act as elastomeric units within the total polypeptide. The elasticity of the monomeric units is believed to result from a series of β-turns in the protein's secondary structure. A β-turn is a 10-atom hydrogen-bonded ring in which the C═O of amino acid residue i is hydrogen-bonded to the NH of residue i+3. Repetitive β-turns result in elastic β-spiral structures.

The bioelastomers can be prepared with various chosen properties (e.g., range of hydrophobicity) by selecting different amino acids for the different positions of the monomeric units and selecting the required proportion of monomeric units. For example, bioelastomers having a pentapeptide unit of the formula $(R_1\ PR_2R_3G)$ (SEQ ID NO:16) where $R_1$ may be Phe, Leu, Ile, Val, Tyr or Trp; $R_2$ may be Ala and Gly; $R_3$ may be Phe, Leu, Ile, Met, Ala and Val, tetrapeptide repeating units of the formula $(R_1PGG)$ where $R_1$ is defined as above, and analogs thereof are described in U.S. Pat. No. 4,898,926. Residues of the repeating units can be substituted with polar amino acid residues, e.g., Glu, Asp, His, Lys or Tyr. Polynonapeptides are disclosed in U.S. Pat. No. 5,064,430. The specific location of any modification of the polymer is not important as long as the bulk properties of the polymer are maintained. It should be noted that bioelastomeric polypeptide chains containing the repeating units can have tetrapeptide or pentapeptid "monomers" that are permutations of the basic sequence (e.g., poly-VPGVG vs. poly-GVGVP) (SEQ ID NOS:1 and 41). The designation of the repeating unit is somewhat arbitrary since the polymer is not synthesized using the pentapeptide "monomers", but rather is synthesized in vivo by sequential adding of amino acids to a growing peptide chain. Moreover, "incomplete units" can flank regions of a repeating unit, for example, a polytetramer GG-(APGG)$_{10}$-A (SEQ ID NO:31) may equally well be thought of as G-(GAPG)$_{10}$-GA (SEQ ID NO:32) or (GGAP)$_{10}$-GGA) (SEQ ID NO:32). Designation of a material as, for example, poly-WXYZ is therefore intended to encompass all same-sequence permutations (poly-XYZW, poly-YZWX, and poly-ZWXY), unless otherwise stated or clear from the context.

Usually, the sequences of the bioelastic monomer units are chosen for their specific properties which provide for their utility (e.g., in prosthetic devices, drug delivery, etc.) as described in the various patents and patent applications of one of the present inventors. Knowing the sequences and ratios of the monomeric units within the polymer allows one to determine, or at least estimate, the effective $T_t$ of the polymer as described above. It may be emphasized here that any chemical means of changing the mean hydrophobicity of the polymer, such as an acid-base titratible function, dephosphorylation/phosphorylation, reduction/oxidation of a redox couple, etc., can be used to bring about coacervation/dissolution at an estimatable $T_t$.

In general, selection of the sequence of amino acids in a particular monomeric unit and selection of the required proportion of monomeric units can be accomplished by an empirical process that begins with determining (or looking up) the properties of known bioelastomers, making similar but different bioelastomers using the guidance provided in this specification and in the cited patents and patent applications. These units are generally present in the polymer in an amount sufficient to provide elastomeric properties and to adjust the development of elastomeric force of the bioelastomer to a predetermined temperature. Considerable variations in the amino acids that are present at various locations in the resulting polymer is possible as long as the multiple β-turns with intervening suspended bridging segments are retained and the desired properties for a particular application are maintained. For this reason it is preferred that at least 50% of the polypeptide is formed from the indicated monomeric units, more preferably at least 70%, even more preferably at least 90%. Nevertheless, it is possible to prepare polypeptides in which these monomeric units are interspersed throughout a larger polypeptide that contains peptide segments designed for other purposes. For example, the bioelastomer can contain naturally occurring sequences which are components of connective tissue. There can be insertions of, for example, single amino acids between monomeric units, substitutions of one amino acid for another in an occasional monomer, or inclusion of different polypentapeptide, polyhexapeptide or polytetrapeptide sequences which can be added to increase strength, elastic modulus and ease of handling. The bioelastic units of the invention can be attached to or interspersed among other types of molecules, which molecular units can impart functions to the polymer such as biological activity, chemotaxis, protease, or nuclease susceptibility. Such molecules include, but are not limited to, peptides, proteins, nucleic acid, DNA, RNA, carbohydrates and lipid chains. As disclosed in earlier U.S. patents, additional properties, e.g. strength, specific binding, are imported to bioelastomeric materials by compounding the repeating elastic units to a second material with greater strength or with the desired property as disclosed in U.S. Pat. Nos. 4,474,851 and 5,064,430. Such compounding can be oriented in the backbone of the polymer by preparing copolymers in which bioelastic units that form fl-turns are interspersed among polymer units providing a desired property, e.g. cell adhesion sequences for appropriate tissue cells. By adding to the protein-based polymer a cell attachment sequence such as Gly-Arg-Gly-Asp-Ser-Pro (GRGDSP) (SEQ ID NO:19) from fibronectin to result in, for example, the elastic matrix $X^{20}$-poly[40 (GGAP),(GRGDSP)](SEQ ID NOS:18 and 19), a matrix which was refractory to cell adhesion now promotes cell adhesion, cell spreading, and growth to confluence in vitro. In general, these sequences can be added covalently and sequentially (e.g., in the case of peptides during biosynthesis) or as side chains to provide for the desired properties. Alternatively, the bioelastomer can be modified after biosynthesis.

A wide variety of genes or gene fragments are useful in forming the fusion sequences with the bioelastic sequences. Any selected, desired DNA sequence can be used as long as the bulk properties of the resulting bioelastomers are not impaired. Desired peptides or proteins can include any peptide or protein useful for human or veterinary therapy, diagnostic or research applications in any expression system. For example, hormones, cytokines, growth or inhibitory factors, enzymes, modified or wholly synthetic proteins or peptides can be produced according to this invention. For example, these may include IL-1, MIP-1α, IL-6, M-CSF, IL-2, IL-3, IL-4, IL-5, LIF, MIF (macrophage inhibitory factor), or a variety of small peptides of random sequence. The ratio of these other molecular units to the bioelastic monomer residue can range from 1:2 to 1:5000. Preferably the ratio is 1:10 to 1:100. The upper limit on the number and kind of substituents is influenced by the ability of the elastic polymer to fold/assemble properly to attain a beta-spiral in the relaxed state.

Fusion sequences can be prepared in a number of different ways. For example, the selected peptide can be fused to the amino terminus of the bioelastomer, to the carboxyl terminus, or within the body of the bioelastomer. Small peptide sequences can be fused to either terminus of the bioelastomer to produce them in a structurally unconstrained manner. Fusing a selected peptide within the bioelastomer constrains the peptide at both ends, reducing the degrees of conformational freedom of the peptide, and consequently reducing the number of alternative structures taken by the peptide. The inserted peptide can be bound at each end by cysteine residues, which may form a disulfide linkage and further limit the conformational freedom of the inserted peptide. This may be advantageous for use of the peptides in screening for bioactive peptide conformations and other assays. Additionally, the fusion of a peptide within the bioelastomer molecule protects it from the actions of *E. coli* amino- and carboxyl-peptidases. The location of a random or systematic substituent in the bioelastic polymer, with respect to the monomer residue side-chain position, is not critical so long as a beta-spiral is not prevented from forming in the relaxed state. Preferred positions for the various peptides of the invention are as taught in the patents and pending applications from the laboratory of the present inventor in this area, which have been incorporated by reference.

Additional amino acid residues can be optionally interspersed within the polymer to enable covalent linkage of the bioelastic polymer to a surface or other molecule, e.g., lipid, DNA, etc. by methods known in the art. For example, cysteine can be introduced into the polymer to allow for linkage via disulfide bridges or lysine can be introduced for enzymatic linkage to a surface. The reactive linking groups are preferably at the N-terminal portion of the molecule. In such embodiments, covalent attachment occurs between a functional group in the bioelastomer and a functional group in the material that forms the surface, which can itself be a different bioelastomer, such as those described in the prior art. Attachment of bioelastomers to surfaces and various coating processes for surfaces are described in various of the patents cited in the Background section of this specification.

The fusion sequence can optionally contain a linker peptide between the bioelastomer and the selected peptide or protein. This linker provides, where needed, a selected cleavage site or a stretch of amino acids capable of preventing steric hindrance between the bioelastomer and the selected peptide or protein. This linker sequence can encode, if desired, a polypeptide which is selectably cleavable or digestible by conventional chemical or enzymatic methods. For example, the selected cleavage site can be an enzymatic cleavage site. Examples of enzymatic cleavage sites include sites for cleavage by a proteolytic enzyme, such as enterokinase, Factor Xa, trypsin, collagenase, and thrombin. Alternatively, the cleavage site in the linker can be a site capable of being cleaved upon exposure to a selected chemical, e.g., cyanogen bromide, hydroxylamine, or low pH.

Cleavage at the selected cleavage site enables separation of the selected protein or peptide from the bioelastomer fusion protein to yield the peptide or protein (or the bioelastomer) which can then be obtained in purified form, free from any polypeptide fragment of the bioelastomer (or fusion peptide) to which it was previously linked. Any desired cleavage site, of which many are known in the art, may be used for this purpose. As described above, the optional linker sequence can serve a purpose other than the provision of a cleavage site. The linker may also be a simple amino acid sequence of a sufficient length to prevent any steric hindrance between the bioelastomer and the selected heterologous peptide or protein. Whether or not such a linker sequence is necessary will depend upon the structural characteristics of the selected peptide or protein and whether or not the resulting fusion protein is useful without cleavage. For example, since bioelastomers can be selected to be substantially inert, the fusion protein may itself be useful as a therapeutic or as a vaccine without cleavage of the selected protein or peptide therefrom.

A secretory leader sequence, among which many are known in the art, e.g. leader sequences of phoA, MBP, β-lactamase, can also be operatively linked in frame to the bioelastomer to enable the expression and secretion of the mature protein into the bacterial periplasmic space or culture medium. For example, this leader sequence can be fused to the amino terminus of the bioelastomer molecule. It is expected that this fusion sequence construct when expressed in an appropriate host cell would be expressed as a secreted protein.

In its broadest aspect, the method of the present invention provides for overexpressing a bioelastic polypeptide in a host cell. The terms peptide, polypeptide and protein are used interchangeably herein. By "overexpressing" it is meant the production of large amounts of peptides or proteins in certain host cells which normally express limited amounts of such peptides or proteins. Generally, the polypeptide is expressed as at least 40% of the total cellular protein of the host cell, preferably at least 60% of the total cellular protein of the host cell, preferably at least 80% of the total cellular protein of the host cell, preferably at least 90% of the total cellular protein of the host cell. The term "nucleic acid" encompasses deoxyribonucleic acid (DNA), ribonucleic acid (RNA), and oligonucleotides, whether biochemically or chemically synthesized. As described above, bioelastomers comprise repeating units which have been described in detail in the patents and patent applications of the present inventor.

In a first step of the present method, a nucleic acid encoding a bioelastic polypeptide is introduced into a host cell. A variety of nucleic acid molecules incorporating sequences encoding the above-described bioelastomers can be constructed for expressing the bioelastomer according to this invention. At a minimum a desirable DNA sequence comprises the sequence described above, in association with, and under the control of, an expression control sequence capable of directing the expression of the bioelastomer in a desired host cell. For example, where the host cell is an *E. coli* strain, the DNA molecule desirably contains a promoter which functions in *E. coli*, a ribosome binding site, and optionally, a selectable marker gene and an origin of replication if the DNA molecule is extra-chromosomal. Numerous bacterial expression vectors containing these components are known in the art for bacterial expression, and can easily be constructed by standard molecular biology techniques. Similarly known yeast, plant, and mammalian cell vectors and vector components may be utilized where the host cell is a yeast cell, a plant cell, or a mammalian cell.

The nucleic acid is operably linked to regulatory regions. By "operably linked" is meant in proper reading frame and orientation, as is well understood by those skilled in the art. Typically, the bioelastic polymer gene will be inserted downstream from a promoter and will be followed by a stop codon, although production as a fusion protein as described above can be used, if desired. In general, host-cell-specific sequences improving the production yield of the bioelastic polymer will be used, and appropriate control sequences will be added to the expression vector, such as enhancer sequences, polyadenylation sequences, and ribosome binding sites.

Techniques known in the art are used to manipulate the genetic information for their effective expression in the appropriate host organism (see, for example, Sambrook et al., (1989) Molecular Cloning: A Laboratory Manual, Second Edition, Cold Spring Harbor, New York; Deguchi et al., (1993) Mat. Res. Soc. Symp. Proc., 292:205–210; Capello, J. (1992) in Review Protein Engineering Biomaterial, Curr. Opin. Struct. Biol., 2:582–586; McPherson et al. (1992); Perbal, B. (1988) In A Practical Guide to Molecular Cloning, 2nd Ed., John Wiley & Sons NY; Ausubel, F. M. (1989) In Current Protocols in Molecular Biology, Vols 1 & 2, John Wiley & Sons NY). The primary tools that make this possible are known in the art and include enzymes capable of cleaving, joining, copying and otherwise modifying polynucleotides. Recombinant DNA can be used to create synthetic genes encoding multiple repeating units of a given peptide sequence and these synthetic genes may themselves be polymerized to create even longer coding sequences, resulting in protein-based polymers of greater length. Genetically encoded amino acids are generally divided into four families: (1) acidic=aspartate, glutamate; (2) basic= leucine, arginine, histidine; (3) non-polar=alanine, valine, leucine, isoleucine, proline, phenylalanine, methionine, tryptophan; and (4) uncharged polar=glycine, asparagine, glutamine, cystine, serine, threonine, tyrosine. Phenylalanine, tryptophan, and tyrosine are sometimes classified jointly as aromatic amino acids. Most of these amino acids are encoded by more than one different codon. The nucleic acids encoding the bioelastic polymer can be modified to contain different codons to optimize expression in the selected host cell, as is known in the art. Vectors allowing the introduction of this information into the host organism in a suitable manner for expression are also known in the art.

For example, DNA fragments having restriction sites at their proximal ends and encoding bioelastomeric polypeptides can be synthesized, using oligonucleotides designed to have appropriate nucleotides at their 5' proximal ends that form restriction sites when double-stranded, and have complementarity at their 3' ends sufficient to promote annealing and extension using a polymerase (usually by PCR). The PCR technique uses the oligonucleotides as primers. This method entails repeated cycles of target DNA denaturation, primer hybridization, and extension with a DNA polymerase to obtain DNA fragments of the expected length. The degree of amplification of a target sequence is controlled by the number of cycles that are performed. Given that the average efficiency per cycle ranges from about 65% to 85%, 25 cycles produce from 0.3 to 4.8 million copies of the target sequence. The PCR method is described in a number of publications, including Saiki et al., Science (1985) 230:1350–1354; Saiki et al., Nature (1986) 324:163–166; and Scharf et al., Science (1986) 233:1076–1078. Also see U.S. Pat. Nos. 4,683,194; 4,683, 195; and 4,683,202.

This approach can be employed to provide DNA fragments that can be incorporated into expression vectors at appropriate restriction sites for their expression in a host in large quantities. Alternatively, shorter oligonucleotides encoding bioelastomer monomer units can be ligated to each other for expression. Using this approach, several levels of complexity are possible. 1.) A single pair of oligonucleotides can be annealed and ligated to give a concatemer with each tandem repeat of the monomer having an identical sequence. 2.) Two or more pairs of oligonucleotides can be used, each with a different composition of allowable codons but maintaining pair-to-pair overlap complementarity. These can be annealed separately and ligated together, or both annealed and ligated as a single mix. This results in the formation of a concatemer gene with a corresponding level of codon diversity. 3.) A single pair of "degenerate" oligonucleotides can be synthesized each with the appropriate mix of bases at the codons' third positions to reflect host codon preference.

Adaptor oligonucleotides are added to the ligation reactions to select and clone concatemers (multimeric sequences). Generally the concatemers will be of a size that can be easily sequenced using flanking primers (e.g., 300–400 bp). The adaptor oligonucleotides can also be used to create terminal restriction enzyme recognition sites that allow excision of the gene for further multimerization to the desired size range (e.g., 150 catemers) or for modification by addition of sequences encoding fusion proteins or additional amino acids as described above. Additional adaptor oligonucleotides can be included in this ligation reaction to allow cloning of the multimer gene into the proper vector for expression in the host system. There appears to be no upper limit to the molecular weight of useful polymers. Polymers containing tip to about 250 pentamers have been synthesized in E. coli using recombinant DNA methods. Typical polymers contain at least 5, preferably at least 10, more preferably at least 20, tetrapeptide or pentapeptide monomers, and because of poor solubility in aqueous solvents, usually contain fewer than 1000, usually fewer than 500, of such units when the polymer is used for biological uses.

An expression cassette can be constructed which will include the transcriptional initiation region, the coding sequence of the gene encoding a bioelastic polymer under the transcriptional regulatory control of the transcriptional initiation region, the initiation codon, and the translational stop codon, followed by the transcriptional termination region, which will include the terminator, and may include a polyadenylation signal sequence, and other sequences associated with transcriptional termination. The direction is 5'-3' in the direction of transcription. The transcriptional initiation region which includes the RNA polymerase binding site (promoter) may be native to the host or may be derived from an alternative source, where the region is functional in the host. The 3' termination region may be derived from the same gene as the transcriptional initiation region or a different gene. The cassette will usually be less than about 10 kb, frequently less than about 6 kb, usually being at least about 1 kb, more usually being at least about 2 kb.

Other sequences not specifically identified above, or perhaps not yet identified or published could be incorporated into the bioelastic polymers and, based on the above description, one of skill in the art will be able to select and identify, or, if desired, modify, a DNA sequence for use in this invention without resort to undue experimentation. Alternatively, polynucleotides encoding bioelastomers can be synthesized chemically by methods known in the art or ribonucleic acid can be used to transform cells.

After constructing the nucleic acid encoding the desired polypeptide sequence, it is artificially inserted into a host organism by methods known in the art. For example, calcium phosphate-mediated transfection, electroporation, or liposome-mediated transfection etc. can be used. To produce the bioelastic polymer, the host cell is either transformed with, or has integrated into its genome, a nucleic acid comprising a sequence encoding the bioelastic polymer. The host can be eukaryotic, e.g. yeast, plant, or prokaryotic, e.g. bacteria. Usually, the host will be microbial, where the resulting protein can then be purified, often in large amounts, from cultures grown in fermentation reactors.

The host cell is grown under known conditions suitable for protein production. Preferably, the cells are grown in the absence of inducers, such as isopropyl β-D-thiogalactopyranoside (IPTG), for gene expression. For example, when the recombinant gene is under the control of a β-galactosidase promoter, prior art methods required the use of IPTG, the inducer normally associated with this inducible promoter, for high levels of recombinant gene expression. This type of inducer is not only expensive, but also is toxic to the cell resulting in lower protein yields compared with methods of the present invention which do not require the addition of inducers.

Various strains of E. coli (e.g., HB101 and W3110) are well-known as host cells in the field of biotechnology. Various strains of B. subtilis, Pseudomonas, and other bacteria may also be employed in this method. Many strains of yeast and other eukaryotic cells known to those skilled in the art may also be useful as host cells for expression of the polypeptides of the present invention. For example, Saccharomyces cerevisia strain EGY-40 can be used as a host cell in the production of various proteins. It could be preferably used instead of E. coli as a host cell in the production of any of the proteins exemplified herein. Similarly, known mammalian cells or plant cells can be employed in the expression of these fusion proteins.

Crop production of the bioelastomers is also an economically viable alternative. *E. coli* and chloroplasts have interchangeable transcriptional/translational machinery (Gruissem and Zurawski, (1985) EMBO J. 4:3375–3383; Boyer and Mullet, (1986) Plant Molecular Biology 6:229–243) and bacterial genes driven by bacterial promoters have been expressed in chloroplasts (Daniell and McFadden, (1987) Proc Natl. Acad. Sci. USA 84:6349–6353). Vectors for transfecting plant cells are known in the art and may optionally allow for parallel expression of a marker gene, such as chloramphenicol acetyl transferase (cat) or β-glucuronidase (uid A), or contain a strong promoter or an enhancer, etc. (Daniell and McFadden, (1991) Plant Cell Reports 9:615–619; Daniell, H., et al., (1990) Proc. Natl. Acad. Sci. USA 87:88–92; Ye, G.N., et al., (1990) Plant Mol. Biol. 15:809–820; Daniell, H., (1993) Methods Enzymol. 217:536–556). Techniques for transforming plant cells with nucleic acid constructs include microinjection, direct DNA uptake using polyethylene glycol, electroporation, viral infection, and transformation with Agrobacterium. Methods for transforming plants are known in the art (Shimamoto, K., et al. (1989) Nature 338:274–277; Datta, S. K., et al. (1990) Bio/Technology 8:736–740; Cristov, P., et al. (1991) Bio/Technology 9:957–962; Gordon-Kamm, W. J., et al. (1990) The Plant Cell 2:603–618; Fromm, M. E., et al. (1990) Bio/Technology 8:833–839; Vasil, V., et al. (1992) Bio/Technology 10:667–674; Weeks, J. T., et al. (1993) Plant Physiol. 102:1077–1084; Somers, D. A., et al. (1992) Bio/Technology 10:1589–1594; Bower, R. and Birch, R. G. (1992) Plant J. 2:409–416; Kung, S. and Wu, R. (1993) Transgenic Plants Engineering and Utilization 1:382; Daniell, H. (1993) Methods in Enzymol. 217:536–556).

Expression in plant cells is achieved using a gene construct prepared and used to transform plant cells. The transformed plant cells may be cells in culture, may be present as a disorganized mass in callus, leaf explants, or shoot cultures, or may be a post-transformation differentiated plant or plant part, such as seeds, leaves, roots, or the like. The foreign nucleic acid will normally be present in all or substantially all of the cells of the plant tissue, but expression may be limited to particular cells or particular times in the development of the plant.

Where the expression cassette is to be transformed into plant cells by means of Agrobacterium, the cassette will be bordered usually within at least about 1 kb by the right and/or left T-DNA borders. These borders may be obtained from any Ti- or Ri-plasmid and may be joined to the expression cassette by conventional ways. The expression cassette may be constructed so as to be directly transferred from a plasmid other than a Ti- or Ri-plasmid or may become integrated into the T-DNA region of a Ti- or Ri-plasmid through homologous recombination. Thus, the expression cassette could have DNA sequences at one or both borders of the expression cassette homologous with sequences present in the T-DNA region of the Ti- or Ri-plasmid.

The expression cassette will normally be carried on a vector having at least one replication system. For convenience, it is common to have a replication system functional in *E. coli* such as ColE1, pSC101, pA-CYC184, or the like. In this manner, at each stage after each manipulation, the resulting construct may be cloned, sequenced, and the correctness of the manipulation determined. In addition, or in place of the *E. coli* replication system, a broad host range replication system may be employed, such as the replication systems of the P-1 incompatibility plasmids, e.g., pRK290. These plasmids are particularly effective with Ti-plasmids, either armed or disarmed, for transfer of T-DNA to the plant species host.

In addition to the replication system, there will frequently be at least one marker present, which may be useful in one or more hosts, or different markers for individual hosts. That is, one marker may be employed for selection in a prokaryotic host, while another marker may be employed for selection in a eukaryotic host, particularly the plant species host. The markers may be protection against a biocide, such as antibiotics, toxins, heavy metals, or the like; or complementation, imparting prototropy to an auxotrophic host. Various genes which may be employed include neomycin phosphotransferase (NPTII), hygromycin phosphotransferase (HPT), chloramphenicol aminotransferase (CAT), nitrilase, gentamicin resistance gene, etc. For plant host selection, markers of particular interest include NPTII, providing kanamycin resistance or G418 resistance, HPT, providing hygromycin resistance, CAT, providing chloramphenicol resistance, etc.

If the protein accumulates in the cytoplasm of a cell it may be released by conventional cell lysis techniques and purified by conventional procedures including selective precipitations, solubilizations and column chromatographic methods. If a secretory leader is incorporated into the fusion molecule substantial purification is achieved when the fusion protein is secreted into the periplasmic space or the growth medium. Where the expression product of the gene is to be located in other than the cytoplasm, the gene will usually be constructed to include particular amino acid sequences which result in translocation of the product to a particular site, which may be an organelle, such as the chloroplast, mitochondrion or nucleus, the cell plasma membrane, or may be secreted into the periplasmic space or into the external environment of the cell. Various secretory leaders, membrane integrator sequences, and translocation sequences for directing the peptide expression product to a particular site are described in the literature. See, for example, Cashmore et al., Biotechnology (1985) 3:803–808, Wickner and Lodish, Science (1985) 230:400–407.

One of the unique advantages in expressing polymers within organelles is that organelles can be isolated before preparing a protein extract resulting in a significant level of purification. For example, chloroplasts can be isolated by homogenization of the tissue in an isotonic buffer and pelleted by low speed centrifugation. Chloroplasts can then be lysed in a hypotonic buffer to release the elastic and plastic protein-based polymers. In addition, exposure of polymers to alkaloid is minimized by expressing them inside chloroplasts. Proteins can also be extracted from intercellular spaces by a simple vacuum infiltration-centrifugation procedure. This procedure washes out contents of the intercellular space and reduces exposure of polymers to alkaloids.

After synthesis, the polymer is usually dissolved in an aqueous medium as a first step in the purification. The media employed may include small amounts of polar organic solvents, usually less than 40 volume percent, more usually less than about 10 volume percent. The solutions can be buffered at a pH in the range from about 6 to 9, more usually from about 7 to 8.5. Various buffers may be employed, such as phosphate, Tris, or the like. Methods for providing expressed proteins in solution are known in the art. For example, methods for providing bacterial lysates and plant extracts are described by Scopes, R. K. (1987) in Protein Purification, Springer Verlag, New York. The expressed protein can be released from the host cell by applying osmotic shock or freeze/thaw treatments to the cell before further purification by conventional means. If a secretory leader is employed in the bioelastic polymer construct, the protein can be recovered from a periplasmic extract or from the cell culture medium. Conventional purification techniques (Scopes, 1987) such as ion exchange chromatography, affinity chromatography, gel filtration, preparative gel electrophoresis etc. can be used in conjunction with methods exploiting the characteristic properties of the bioelastic polymers.

As yet a further step in the above methods, the bioelastic polymer can be cleaved from additional peptide fragments using conventional means, if necessary. For example, factor Xa, can be employed for cleavage. Bioelastomeric polymers having no methionines in their sequence can be expressed as recombinant proteins designed to incorporate a methionine residue at a fusion junction. Preferably, there would be no methionines in the bioelastomeric polypeptide, when cleavage of the fusion protein is with cyanogen bromide (G. Allen, (1989) "Sequencing of Proteins and Peptides," in Laboratory Techniques in Biochemistry and Molecular Biology; R. H. Bundon et al. Eds, Elsevier, New York,). Alternatively, less expensive enzymatic means of cleavage, such as cleavage following a lysine or arginine by trypsin, can be employed to remove peptides where lysine or arginine is not present within the bioelastomer or protein of interest.

One potential problem associated with the expression of protein-based polymers may be the presence of methionine encoded by the start codon of the polymer gene, which may modify reactivity of an elastomeric polypeptide although, in terms of hydrophobicity, it is very similar to a valyl residue. This problem can be overcome by chemical cleavage of the peptide after isolation or by targeting the polypeptide using a suitable transit peptide sequence. Several transit peptide sequences have been successfully used to target foreign proteins (Cheng et al. (1988) Proc. Natl. Acad. Sci. USA 85:391–395). The transit peptide is cleaved as the protein is transported into, for example, the chloroplast or intercellular spaces, thereby simplifying purification.

In addition to providing high levels of the selected peptide or bioelastomer upon cleavage from the fusion protein for therapeutic or other uses, the fusion proteins may themselves be useful as therapeutics provided the bioelastomer is not antigenic to the animal being treated. Further, the bioelastic fusion proteins may provide a vehicle for the delivery of bioactive peptides. As one example, since bioelastomers are generally not antigenic in mammals, a fusion protein with the bioelastomer may be useful as a vehicle for delivering to humans the biologically active peptide to which the bioelastomer is fused.

The bioelastomer may or may not be cross-linked, depending on the manner of its ultimate use. For example, if the bioelastomer is used as a surface coating on a second material that provides appropriate mechanical properties, cross-linking is not necessary to proved mechanical strength. Cross-linking of a polymer solution to form a matrix, whether formed from elastic β-spiral structures or from reversible plastic β-spiral structures, can be performed using various cross-linking process. For example, U.S. Pat. No. 4,589,882, incorporated herein by reference, teaches enzymatic cross-linking by synthesizing polymers having enzymatically cross-linkable units. This type of cross-linking can occur in vivo. These bioelastic polymers are described in the various patents and other documents listed above that arose in the laboratories of the present inventors. Additionally, cross-linking by irradiation is described in detail in nearly all of the prior patents arising from the laboratories of the inventor, which have been incorporated by reference above. Cross-linking provides mechanical strength and rigidity to the polymer, and increasing amounts of cross-linking are appropriate for increasing demands of rigidity. Typical amounts of cross-linking provide one cross-link for every 5–100 tetrapeptide or pentapeptide units. Polymers described in this specification that are prepared by irradiation cross-linking are identified as, for example, "$X^{20}$-poly(GGAP) (SEQ ID NO:14)," which refers to a polymer prepared from GGAP tetrapeptide units (SEQ ID NO:14) that has been γ-irradiated with a 20 Mrad dose of cobalt-60 radiation to form the cross-links which result in an insoluble matrix.

The invention now being generally described, the same will be better understood by reference to the following examples, which are provided for purposes of illustration only and are not to be considered limiting of the invention.

EXAMPLES

Example 1

Expression and Purification of Poly(GVGVP)$_{120}$ in E. coli

The (GVGVP)$_{120}$ was constructed using synthetic oligonucleotides having the sequence depicted in FIG. 1 (SEQ ID NOS:26–29). The oligonucleotides were flanked with sequences containing the BamH 1 (GGATCC) (SEQ ID NO:50) and PflM 1 (CCAGGCGTTGG) (SEQ ID NO:20) restriction endonuclease recognition sites. This nucleic acid was inserted into the plasmid pUC118 and used to transform E. coli. After isolating the amplified plasmid, the sequence of the gene insert was verified by DNA sequence analysis (Sambrook et al., Molecular Cloning: A Laboratory Manual, Second Edition, Cold Spring Harbor, New York (1989)).

This 10 mer gene was then used as a modular unit for constructing longer genes encoding (GVGVP)$_n$ of higher molecular weights. Plasmid containing the 10 mer gene was prepared and digested with PflM 1. The PflM 1 (GVGVP)$_{10}$ gene fragments were then purified and used in subsequent ligation reactions to form polymers of [(GVGVP)$_{10}$]$_n$ (SEQ ID NO:43). Also, separate adaptor oligonucleotides with unique restriction sites were added to this ligation reaction to allow the subsequent cloning of the concatenated gene fragments. These adaptor oligonucleotides were added at a ratio that would favor the recovery of high molecular weight "concatemers".

For recovery and cloning of individual length concatemer genes, the ligation mixture was digested with BamH1 then electrophoresed through an agarose slab gel to achieve separation of the various molecular weight sizes. Slices corresponding to different size ranges then were removed from the gel, the DNA was recovered, and then cloned into plasmid pUC118 (Urry et al. "Elastic and Protein-based Polymers: Potential for Industrial Uses, (Am. Chem. Soc.) Div. Polym. Mat.: Sci & Engr., "Industrial Biotechnological Polymers," Washington D.C., 1994). Gene inserts into this plasmid were analyzed by restriction endonuclease digestion and accurately sized by agarose gel electrophoresis adjacent to a concatemer "ladder". To achieve expression of a native protein-based polymer in E. coli, a concatemer gene encoding (GVGVP)$_{120}$ (SEQ ID NO:42) was subcloned from pUC118 into the expression vector pET-11d (Novagen, Inc.) as a Nco1 to BamH 1 fragment.

Culture conditions: The bacterial host used for cloning and expression was E. coli K12 strain HMS174 (F$^-$ recA rk$_{12}$$^+$ Rif[1]) containing a lysogen DE3 in its genomic DNA. DE3 is a lambda derivative that has the immunity region of phage 21 and carries a DNA fragment containing the lacI gene, the lacUV5 promoter, the beginning of the lacZ gene and the gene for T7 RNA polymerase (F. W. Studier and B. A. Moffat (1986) *J. Mol. Biol.* 189:113). Gene expression was studied in 9 samples each grown in LB or TB medium for different durations. Cultures were grown in either Luria broth (LB-10 g bacto tryptone, 5 g bacto yeast extract and 10 g NaCl per 1 lt distilled water) or in Terrific broth (TB-12 g bacto tryptone, 24 g bacto yeast extract, 4 ml glycerol and 100 ml TB salts containing 0.17 M $KH_2PO_4$ and 0.72 M $K_2HPO_4$, in 1 lt distilled water) in the presence or absence of ampicillin (100 μg/ml) at 37° C. After 3 hours of growth (at an O.D. of 0.8), control cultures were induced with 1 mM isopropylthio-β-D-galactoside (IPTG) and continued to grow for different durations; cells were stored at 4° C. at the end of the time course.

SDS-gel electrophoresis: SDS-polyacrylamide gels were prepared and electrophoresed according to Laemmli (U. K. Laemmli (1970) *Nature* 227:680). Form each sample, 1.5 ml culture was centrifuged at 12000× rpm for 30 seconds. The supernatant was discarded and the cell pellet was washed once in 500 μl of Tris.Cl (50 mM, pH 7.6) resuspended in 100 μl of distilled water. From this, 20 μl sample was taken into a fresh tube, equal volume of 2× SDS gel loading buffer (100 mM Tris.Cl-pH 6.8, 200 mM dithiothreitol, 4% SDS, 0.2% bromophenol blue and 20% glycerol) was added and the sample was boiled for 5 minutes. Samples were loaded on the gel along with high range protein marker (Bio-Rad) and partially purified polymer standard. After electrophoresis, protein bands were visualized by a negative staining technique with $CuCl_2$ (C. Lee, A. Levin, and D. Branton (1987) *Anal. Biochem.* 166:308). Cell lysates of both TB and LB grown cultures were separated on SDS-polyacrylamide gels.

Polymer protein was seen by negative staining around 60 kDa. The pattern of polymer production was the same in both gels, although the quantity of polymer was several fold more in TB grown cultures (uninduced). The amount of polymer in uninduced—6 hour sample was approximately comparable to that of the induced—6 hour sample. However, there was a dramatic increase in the expression of polymer in uninduced cultures grown for 24 hours over induced cultures of the same age. This increase was more pronounced in TB grown cultures compared to LB grown cultures which is not surprising because it is known that in TB grown cultures, copy number of the plasmid increases by 4–7 fold and the cell density increases by 10 fold over those of the LB grown cultures (K. D. Tartof and C. A. Hobbs (1987) *Bethesda Res. Lab. Focus* 9:12). In contrast, the amount of polymer produced in induced cultures was negligible accompanied by irregular shapes of cells (see electron micrographs in FIG. 1). The decrease in polymer production in induced cells could be directly correlated with the loss of plasmid. No plasmid DNA was found in cells induced with IPTG beyond 6 hours of growth. Brosius (J. Brosius (1984) *Gene* 27:161) reported that induction of trp/lac (tac) hybrid promoter with 1 to 5 mM IPTG in *E. coli* strain RB 791 (lac repressor overproducing strain) caused reduced cell growth rate leading to cell lysis. This is further supported by Masui's (Y. Masui, T. Mizuno and M. Inouye (1984) *Bio/Technology* 2:81) findings that the growth rate of *E. coli* T19 cells induced with IPTG was reduced after 5–6 hours. The highest expression of protein is noticed in uninduced cultures at 24 hours, followed by a gradual reduction in cultures grown beyond 24 hours. This is due to cell lysis after 24 hours as evident under light microscopic observation.

Transmission electron microscopy: The same samples used in SDS-PAGE were used for electron microscopy. Cells were washed with double distilled water and pre-fixed in 3% glutaraldehyde (final concentration) in 0.05 M cacodylate buffer for 3 hours at 4° C. Then, cells were washed in 0.05 M cacodylate buffer for 12 hours to remove excess glutaraldehyde. Post-fixation of the cells was done with 1% Osmium tetroxide (final concentration) in cacodylate buffered solution (0.05 M) for 1.5 hours followed by a buffer wash to remove the unbound osmium. Pellets were kept as dry as possible and solidified with 2% agarose. From the solidified pellets, about 1 $mm^3$ size blocks were minced with razor blade and dehydrated in a graded series of ethanol (30%, 50%, 70%, 80%, 90% and 100%) followed by propylene oxide treatment. The samples were embedded in Spur's low viscosity epoxy resin for firm tissue (A. R. Spurr (1969) *Ultrastruct. Res.* 26:31). Blocks were trimmed and sectioned on a microtome (Bausch & Lomb stereozoom 4) using glass knives, and silver sections were picked up on copper grids for staining. Sections were stained with heavy metal based solutions like uranyl acetate (1%, pH~4.0) for 40 minutes and lead citrate (pH~12.0) for 2 minutes. Grids were washed in 0.1 N NaOH and in distilled water and dried on filter papers. Specimens were observed under Zeiss transmission electron microscope. Light microscopic studies using oil immersion lens (Carl Zeiss, plan 100/1, 25 oil ph3) showed distinct intracellular inclusion bodies both in induced and uninduced cells at 6 hour growth period. The first inclusion body in a cell is found mostly but not necessarily at one end of the cell but, as the cell growth progressed, the number and size of inclusion bodies increased only in the uninduced cells up to 24 hours, beyond which the cells lyse. In contrast, induced cells grown beyond 6 hours attain irregular shapes without any inclusion body. These results correspond to SDS-PAGE results, where maximum polymer production is observed in 24 hour old TB grown uninduced cultures. Hence, the TEM studies were restricted up to 24 hours in induced and uninduced cultures including the host strain without plasmid as the control.

TEM micrographs taken at different growth durations of induced and uninduced cultures are shown in FIG. 2. At 6 hours, the uninduced cells are rod shaped with smooth cell wall and with several inclusion bodies all along the cell (FIG. 2A), but induced cells appear sick with an irregular cell wall and shape and no well defined inclusion body (FIG. 2B). As growth progressed up to 24 hours, the uninduced cells show a dramatic increase in the number and size of inclusion bodies pushing the cytoplasm aside and occupying the cell volume to a maximum extent possible (FIGS. 2C and 2E). The inclusion bodies are well separated from the cytoplasm although a definite membranous boundary is lacking as reported by others (D. C. Williams, R. M. Van Frank, W. L. Muth and J. P. Burnett (1982) *Science* 215:687 and E.G. Schoner, L. F. Ellis and B. E. Schoner (1985) *Bio/Technology* 3:151). These structures are distinct from the cell cytoplasm by their lighter stain, round to oval shape and poorly infiltered regions showing dense cytoplasm and no inclusion body (FIG. 2D). Host cells not transformed with plasmid DNA show normal cell growth with no inclusion body.

The progression in the number and size of inclusion bodies from 6 hours (FIG. 2A) to 24 hour grown cells (FIGS. 2C, 2E) correlate well with the increase in the amount of polymer protein produced in respective samples on SDS-polyacrylamide gels. Similarly, the absence of inclusion bodies in the induced cells at 24 hours (FIG. 2D) and in plasmid minus host cells (FIG. 2F) is accompanied by the absence of polymer production. From this we could correlate the appearance of inclusion bodies in the transformed *E. coli* to the production of target protein. Similar correlations were made between the amount of inclusion product within the cells to the quantity of chimeric product seen on SDS-polyacrylamide gels in *E. coli* strains overproducing insulin chains A and B (D. C. Williams et al. (1982)). They estimated that at peak production level, the inclusion bodies could occupy as much as 20% of the *E. coli* cellular volume. By visual observation of our micrographs, we estimate the volume occupied by these bodies is more than 90% under optimal conditions. Inclusion bodies are formed when the cloned proteins are synthesized to levels above their solubility or when precipitation of the native protein takes place (J. F. Kane and D. L. Hartley (1988) *Trends in Biotechnol.* 6:95).

Example 2
Expression of Gene Constructs Encoding a Bioelastic Fusion Polymer in *E. coli*

Positive clones in pUC118 described above are subcloned into plasmid pQE-32 (Quiagen, Inc.) as a gene fusion behind a sequence encoding six tandem histidines. Expression using this plasmid results in the production of proteins with an amino-terminal polyhistidine fusion, specifically, MRGSH$_6$GIQTM-(GVGVP)$_n$ (SEQ ID NO:21). This fusion moiety provides the ability to affinity purify the protein by metal-chelate chromatography. The poly(GVGVP) polymers (SEQ ID NO:41) are produced as described in Example 1. The polymer is affinity purified by metal-chelate chromotography by virtue of the presence of the polyhistidine moiety at the N terminus of the polymer. Correct biosynthesis of the polymer is analyzed by showing that the polymer has the requisite glycine, valine and proline at the expected ratios for poly(GVGVP) (SEQ ID NO:41) by amino acid analysis of phenylisothiocyanate (PITC) derivatives of the amino acids which are separated by reverse phase liquid chromatography.

Example 3
Expression of Gene Constructs Encoding a Glutathione-S-Transferase-G-(VPGVG)1$_9$-VPGV Fusion Protein in *E. coli*

The plasmid pEPP-3 has been described by McPherson et al. (Biotechnol. Prog. 1992, 8, 347–352). This plasmid is used to transform *E.coli* and express protein in the absence of IPTG, as described in Example 1.

Example 4
Expression of Elastic Protein-Based Polymer, Poly(GVGVP) in Tobacco Chloroplasts Genes encoding the poly(GVGVP) protein (SEQ ID NO:41) in the range of 150 tandem pentapeptide units are constructed for expression in tobacco systems using synthetic oligonucleotides and PCR, to encode 10 repeating units of the GVGVP (SEQ ID NO:41). FIG. 3 shows the sequence of the gene, comprising optimal codons for tobacco while maintaining maximal coding degeneracy. The gene is constructed using two oligonucleotides, each representing just over half of the gene. The oligonucleotides have complementary 25 base overlaps (dotted underline in figure) at their 3' ends that are extended by the PCR reactions to form the full-length double-stranded sequence. The PCR product is digested with BamH1 and inserted into plasmid pUC119 for sequence confirmation and continued maintenance. The fragment is excised from pUC119 using PflM 1 and self-ligated to form concatemers, with the inclusion of adaptor fragments to terminate multimerization in the desired size range.

The synthetic gene is introduced into chloroplasts of cultured tobacco cells using the Gene Gun, essentially as described by Daniell (Methods Enzymol. 217 (1993) 536–556). After continued growth of transformed cells in MS salt medium in the presence of $^{35}$S methionine, chloroplasts are isolated using a Mini-bead beater (Daniell et al. (1993) Nucleic Acids Res. 21:1503–1504). Soluble chloroplast proteins are obtained by rupturing chloroplasts in hypotonic buffer.

Example 5
Expression of Plastic Protein-Based Polymer Poly (AVGVP), from Tobacco For construction of the gene encoding poly(AVGVP) (SEQ ID NO:34) in the range of 150 repeating units for expression in tobacco, a different concatemeric approach is used. Specifically, two 15 base degenerate oligonucleotides, 5' CCNGCNGTNGGNGTN 3' (SEQ ID NO:22) and 5' CNGGNACNCCNACNG 3' (SEQ ID NO:23), are synthesized (where N=G,A,T or C), each representing one strand of a double-stranded unit encoding the (AVGVP) monomer (SEQ ID NO:34), with codon choice for tobacco. The two strands are offset such that they anneal leaving 4–5 base overlapping ends that are complementary, allowing joining of the 5' ends to the 3' ends. The annealed oligonucleotides, or catemers, are ligated through their complementary ends to form long multimers, or concatemers, as described above for the (GVGVP)$_{10}$ genes. Expression of the bioelastomeric polypeptides its essentially as described above.

Figure 4:
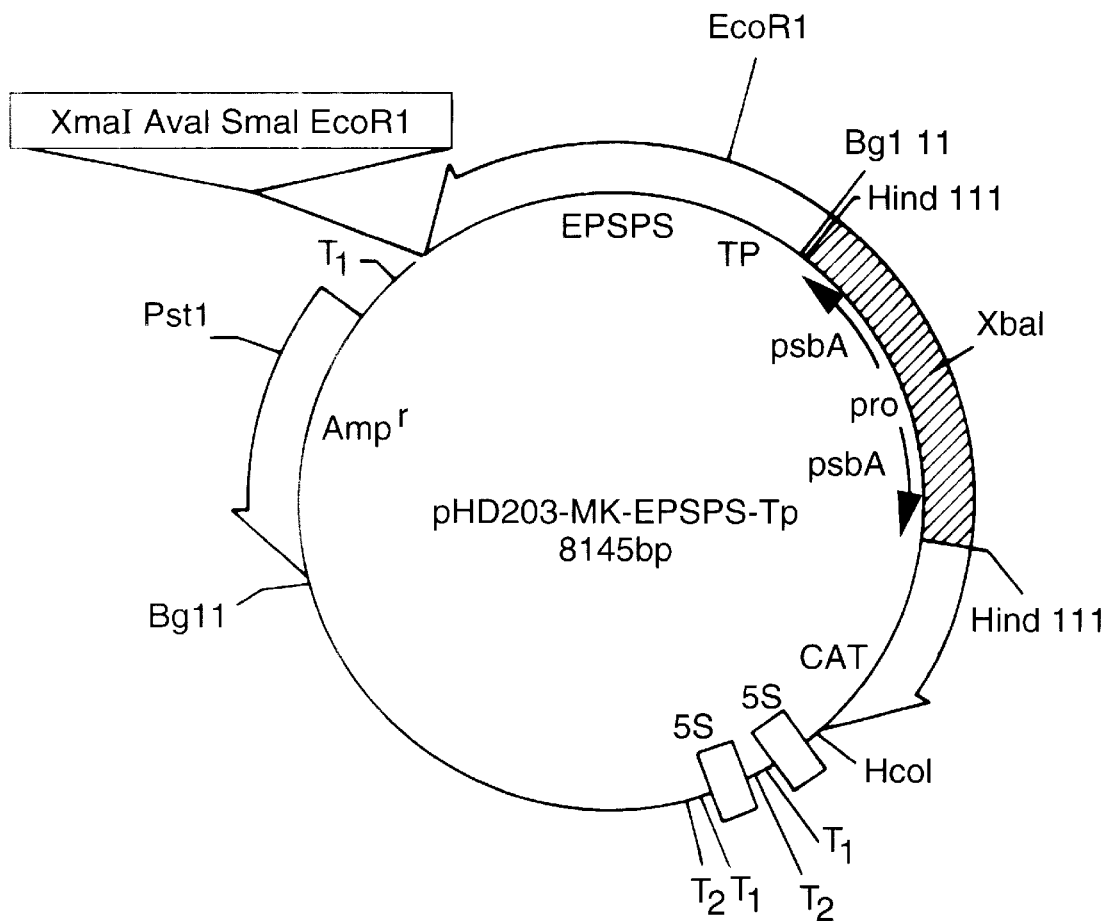
FIG. 4 A map of the plasmid pHD203-GUS-EPSPS (EN/polyA)

Example 6
Expression of poly(VPGVG) After Stable Chloroplast or Nuclear Transformation The plasmid pHD203-GUS-EPSPS (EN/polyA) (see FIG. 4) contains CaMV 35S promoter/enhancer elements driving the aroA gene (coding for EPSP synthase conferring resistance to glyphosate) and flanked at the 3' end by a polyA fragment to stabilize the transcript. The coding sequence for G-(VPGVG)$_{19}$-VPGV (SEQ ID NO:30) (the 20 mer) fused with the gst coding sequence is inserted at the BglII site in pHD203-GUS-EPSPS-(EN/polyA) using adaptors or by filling in the recessed 3' end termini using Klenow fragment of *E. coli* DNA polymerase I. Stable expression is achieved by bombarding the EPSPS vector containing gst-EG20 mer coding sequences into cultured tobacco cells and growing them in the presence of glyphosate. The coding sequences are inserted into the region between rbcL and ORF 52 of the tobacco chloroplast genome in order to accomplish a high frequency of transformation (Svab and Maliga, (1993) Proc. Natl. Acad. Sci. USA 90 913–917).

Transgenic tobacco plants expressing polymers inside chloroplasts are obtained by bombarding leaves from aseptically grown plants with chloroplast vectors. Calli formed on selection media are regenerated. Optimal conditions for selection and regeneration of tobacco chloroplast transgenic plants is known in the art (Svab et al., (1990) Proc. Natl. Acad. Sci USA 87:8526–8530; Staub and Maliga, (1992) The Plant Cell 4:39–45; Svab and Maliga (1993) Proc. Natl. Acad. Sci. USA 90:913–917.

Molecular and Biochemical Analyses of Chloroplast Transformants

Chloroplast DNA is isolated from transgenic plants by methods known in the art. Ethidium bromide stained gels of restriction digested ctDNA preparations are examined to detect additional ctDNA fragments; insertion of the EPSPS/gst-EG20 mer fragment from chloroplast vectors into tobacco ct genomes introduce additional restriction sites into ct genomes of transgenic plants. ctDNA is digested with restriction enzyme and separated by electrophoresis on agarose gels and blotted onto nylon membranes. Fragments containing EPSPS or gst or polymer coding sequences are used as hybridization probes. All transgenic lines are tested for the presence of EPSPS-gst-polymer coding sequences in tobacco chloroplast genomes.

Example 7
Stable Nuclear Expression of Protein-Based Polymers in Transgenic Tobacco The synthetic gst-G-(VPGVG)$_{19}$-VPGV gene cassette (SEQ ID NO:1) (Mc Pherson et al.) is inserted into a pKYLX vector (Schardl et al., (1987) Gene 61:1–11) as follows. The MaeI/EcoR1 fragment containing the cassette is modified to incorporate a new ATG codon through addition to a Xho/Nco1 adapter (5'-TCGAGCCATGG-3 '/3'-CGGTACC-5') (SEQ ID NOS:24 and 44) to the 5' end and moved into pKLYX7.1 as a Xho1/EcoR1 fragment. pKLYX7.2, a derivative of pKLYX7.1 (Daniell et al. (1986) Proc Natl. Acad Sci. USA 83:248–255) wherein the XbaI site has been replaced with an EcoR1 site is employed to receive the gst-G-(VPGVG)$_{19}$-VPGV (SEQ ID NO:30) cassette.

Young, fully expanded tobacco leaves (*Nicotiana tabacum* cv KY 14) are taken from 8-week-old plants and surface sterilized for 10 min with 10% chlorox, followed by 3 min in 70% alcohol and washed 3 times with sterile distilled water. *Agrobacterium tumefaciens*-mediated leaf disk transformation and shoot regenerations are performed as described by Horsch et al. (1985) Science 227:1229–1231). Briefly, putative transformants are selected on MS media containing 300 mg/L kanamycin and 500 mg/L mefoxin as described by Svab et al. (Proc. Natl. Acad. Sci. USA (1990) 87:8526–8530). Kanamycin resistant shoots are transferred to rooting media. Approximately 50 kanamycin-resistant plantlets are selected for analysis. Control plants are transformed with pKYLX7.2 alone.

Putative transformants are verified by Southern hybridization and assayed for NPTII phosphotransferase activity as well as for production of the gst-G-(VPGVG)$_{19}$ -VPGV protein (SEQ ID NO:30) (McPherson et al.). Selected individual transformants are selected to produce a homozygotic individual that is used as an initial progenitor for seeds to be used in field studies. Approximately 1 acre is planted with each type of transgenic tobacco. Smaller plots of vector-only transformed plants and nontransformed plants serve as controls for growth comparison or other assessments. Seedlings are greenhouse propagated and transplants are planted in research plots.

Example 8
Expression of (GGAP)$_{12}$ (SEQ ID NO:45) and (AVGVP)$_{10}$ (SEQ ID NO:35) in *E.coli*

The basic genes encoding (GGAP)$_{12}$ and (AVGVP)$_{10}$ are described in FIG. 5 (SEQ ID NOS:6 and 7). These are constructed using synthetic oligonucleotides. For each gene, two single-stranded oligonucleotides are annealed through a twenty base region (dotted line in figure) of complementarity at their 3' ends. These ends are extended using a Taq polymerase and deoxyribonucleotides in a thermal cycler to create a full-length double-stranded sequence. Each gene has terminal BamHI sites for subsequent cloning into the general purpose vector pUC118. Genes that are successfully cloned into pUC118 are verified by DNA sequence analysis. Positive clones are then used as the source for large-scale preparation of gene fragment for concatenation in the presence of ligase to form multimers, or concatemers, of the basic gene unit. In the case of AVGVP, PflMI sites are used to release the gene fragment from pUC118 by digestion with the corresponding enzyme. PflMI recognizes the interrupted palindrome CCANNNNNTGG (SEQ ID NO:25) and cuts to leave a 3' three base overhang. Consequently, when the purified gene fragments are ligated to eachother, they can only ligate in a head-to-tail fashion therebyt maintaining uniform coding polarity. For the GGAP gene, Bbs-1 sites are used to release the gene fragment from the plasmid. Bbs-1 recognizes the non-palindromic sequence GAAGAC and cuts two bases 3" to the site to leave a 5' 4 base overhang. The Bbs-I sites are arranged so that on digestion with the enzyme, the GGAP coding sequence is released leaving the recognition sites with the plasmid.

In order to clone the concatemer genes, synthetic double-stranded oligonucleotide "adaptors" are added to the ligation reactions. These adaptor oligonucleotides shown in FIG. 6, provide 5' and 3' terminal restriction endonuclease sites needed for cloning the concatemers into the receptor plasmid pUC 118 and for their subsequent sub-cloning into the expression vector pET-11d.

These constructs are used to transform *E. coli* BL21(DE3) or HMS 174(DE3) which is then propagated to produce the gene product as described in Example 1 above.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for overexpressing a bioelastic polypeptide in a prokaryotic host cell, said method comprising:
   (a) introducing into said host cell, a vector comprising a promoter operably linked to a nucleic acid encoding a bioelastic polypeptide comprising pentapeptide, tetrapeptide, hexapeptide or nonapeptide repeating units; and
   (b) growing said host cell to provide for expression of said polypeptide in the inclusion bodies of said host cells, where the volume of said inclusion bodies comprises 40–90% (v/v) of the total cellular volume of said host cell and the amount of inclusion bodies correlates to the amount of polypeptide expressed;
   with the proviso that when said promoter is an inducible promoter said host cells are grown and said polypeptide is expressed in the absence of an inducer normally associated with said inducible promoter.

2. The method of claim 1 where said prokaryotic host cell is *E. coli*.

3. The method of claim 1 wherein the volume of said inclusion bodies comprises at least 60% (v/v) of the total cellular volume of said host cell.

4. The method of claim 1 wherein the volume of said inclusion bodies comprises at least 80% (v/v) of the total cellular volume of said host cell.

5. The method of claim 1 wherein the volume of said inclusion bodies comprises 90% (v/v) of the total cellular volume of said host cell.

6. The method of claim 1 wherein said promoter is an inducible promoter.

* * * * *